United States Patent [19]

Nishi et al.

[11] Patent Number: 5,008,274

[45] Date of Patent: Apr. 16, 1991

[54] CARBOSTYRIL DERIVATIVES AND SALTS THEREOF AND PHARMACEUTICAL COMPOSITION FOR INHIBITING ADHESION OF THROMBOCYTES

[75] Inventors: Takao Nishi; Tetsuyuki Uno; Yasuo Koga; Gil-Namg Chu, all of Tokushima, Japan

[73] Assignee: Otsuka Pharmaceutical Co., Ltd., Tokyo, Japan

[21] Appl. No.: 232,524

[22] Filed: Aug. 16, 1988

Related U.S. Application Data

[63] Continuation of Ser. No. 36,564, Mar. 31, 1987, abandoned.

[30] Foreign Application Priority Data

Apr. 2, 1986 [JP] Japan ................................. 61-76089
Feb. 25, 1987 [JP] Japan ................................. 62-43457
Mar. 16, 1987 [JP] Japan ................................. 62-60770

[51] Int. Cl.$^5$ .................. A61K 31/47; A61K 31/505; C07D 401/12; C07D 403/12

[52] U.S. Cl. .................................. 514/312; 514/247; 514/248; 514/249; 514/252; 514/255; 514/256; 514/259; 514/269; 514/274; 514/300; 514/307; 514/309; 544/235; 544/236; 544/238; 544/284; 544/298; 544/315; 544/316; 544/319; 544/336; 544/353; 544/354; 544/405; 544/408

[58] Field of Search .................. 546/157, 158; 514/312

[56] References Cited

U.S. PATENT DOCUMENTS

| 4,277,479 | 7/1981 | Nishi et al. | 514/312 |
| 4,329,347 | 5/1982 | Müller et al. | 514/312 |
| 4,792,561 | 12/1988 | Walker et al. | 514/312 |
| 4,824,840 | 4/1989 | Banno et al. | 514/218 |

FOREIGN PATENT DOCUMENTS

| 2806721 | 8/1979 | Fed. Rep. of Germany . | |
| 2912105 | 10/1979 | Fed. Rep. of Germany . | |
| 2928583 | 1/1981 | Fed. Rep. of Germany | 546/158 |
| 0032471 | 4/1981 | Japan | 546/158 |
| 0045414 | 4/1981 | Japan | 546/158 |
| 0156263 | 12/1981 | Japan | 546/157 |
| 0009780 | 1/1982 | Japan | 546/158 |
| 0154129 | 9/1982 | Japan | 514/312 |
| 0159778 | 10/1982 | Japan | 546/157 |
| 0059980 | 4/1983 | Japan | 546/158 |
| 0077880 | 5/1983 | Japan | 546/158 |
| 2071094 | 9/1980 | United Kingdom . | |
| 2127402 | 4/1984 | United Kingdom . | |
| WO84/02908 | 8/1984 | World Int. Prop. O. . | |

OTHER PUBLICATIONS

Nishi et al., Chemical Abstracts, vol. 108, No. 167318 (1988).
Yoshizaki et al., Chemical Abstracts, vol. 91, No. 39479 (1979).
Abstract for JP 32471 (4/1/81).
Abstract for JP 156263 (12/2/81).
Abstract for JP 77880 (5/11/83).
Abstract for JP 45414 (4/25/81).
Abstract for JP 59980 (4/9/83).
Abstract for JP 159778 (10/1/82).
Abstract for JP 9780 (1/19/82).
Abstract for JP 154129 (9/22/82).
Abstract for DE 2928583 (1/29/81).
Burger, "Medicinal Chemistry", Interscience Publishers, N.Y. (1960), 2nd Edition, p. 75.
Abstract for JP 54/30183 (3/6/79).
Abstract for JP 54/30180 (3/6/79).

Primary Examiner—Mark L. Berch
Assistant Examiner—E. Bernhardt
Attorney, Agent, or Firm—Finnegan, Henderson, Farabow, Garrett & Dunner

[57] ABSTRACT

A carbostyril derivative or pharmaceutically acceptable salt thereof represented by the following general formula:

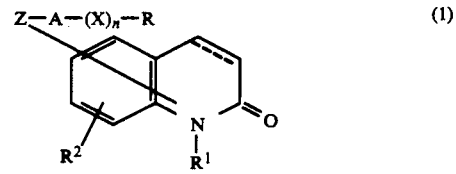

wherein Z, A, XN, R, $R^1$, and $R^2$ are as defined in the specification. These carbostyril derivatives are useful in pharmaceutical compositions for inhibiting adhesion of thrombocytes.

18 Claims, No Drawings

CARBOSTYRIL DERIVATIVES AND SALTS THEREOF AND PHARMACEUTICAL COMPOSITION FOR INHIBITING ADHESION OF THROMBOCYTES

This application is a continuation of application Ser. No. 036,564, filed Mar. 31, 1987, now abandoned.

BACKGROUND OF THE INVENTION

1. Field of the Invention

The present invention relates to carbostyril derivatives and salts thereof. More particularly, the invention relates to the carbostyril derivatives and salts thereof, processes for preparing the same, and a pharmaceutical composition for inhibiting of thrombocyte adhesion containing said carbostyril derivative or salt thereof as the active ingredient.

2. Prior Art

There have been known some carbostyril derivatives and salts thereof having the chemical structural formula similar to those of the carbostyril derivatives and salts thereof represented by the general formula (1) according to the present invention. (Cf. U.S. Pat. Nos. 3,975,391; 3,994,901; 4,022,776; 4,026,897; 4,068,076; 4,145,542; 4,216,220; 4,277,479; British Patent Nos. 1,496,766; 1,496,767; 1,496,768; 1,496,769; 1,496,770; 1,496,871; 1,496,872; 1,496,874; 1,496,875; 1,505,305; 2,071,094; and 2,033,893 and others.)

However, the pharmacological activities of said known carbostyril derivatives are quite different from those of carbostyril derivatives and salts thereof represented by the general formula (1) according to the present invention.

SUMMARY OF THE INVENTION

An object of the present invention is to provide carbostyril derivatives and salt thereof represented by the general formulas (1a), (1b) and (1c).

Another object of the present invention is to provide processes for preparing carbostyril derivatives and salts thereof represented by the general formula (1).

Further object of the present invention is to provide a pharmaceutical composition for inhibiting adhesion of thrombocytes containing said carbostyril derivative or salt thereof as the active ingredient.

Yet, further object of the present invention is to provide a method for inhibiting of thrombocyte adhesion by administering said carbostyril derivative or salt thereof.

DETAILED DESCRIPTION OF PREFERRED EMBODIMENTS

Carbostyril derivatives and salts thereof according to the present invention are represented by the general formula (1),

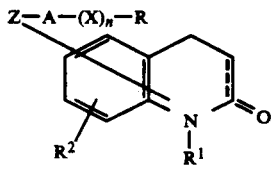
(1)

wherein R is an unsaturated heterocyclic residual group having 1 to 4 hetero atoms selected from the group consisting of a nitrogen atom, an oxygen atom and a sulfur atom; said unsaturated heterocyclic residual group may have 1 to 3 substituents, on the heterocyclic residual ring, selected from the group consisting of an oxo group; a thio group; a phenyl group; a phenyl group which may have 1 to 3 substituents, on the phenyl ring, selected from the group consisting of a lower alkyl group, a halo-lower alkyl group, a halogen atom, a hydroxy group, an amino group, a lower alkylamino group, a carboxy group and a lower alkoxy group; a cycloalkyl group; a phenylthio group; a lower alkyl group; a lower alkyl group having 1 to 2 substituents selected from the group consisting of an amino group, a lower alkylamino group and a carboxyl group; an amino group; a hydroxyl group; a cyano group; a carboxyl group; a lower alkoxycarbonyl group; a phenyl-lower alkyl group which may have hydroxyl groups as the substituents on the phenyl ring; a phenylsulfonyl group which may have lower alkyl groups as the substituents on the phenyl ring; a lower alkoxy-substituted phenyl-lower alkyl group; a lower alkylthio group; a lower alkenyl group; a lower alkoxy group and a pyridyl group;

$R^1$ is a hydrogen atom, a lower alkyl group or a phenyl-lower alkyl group;

$R^2$ is a hydrogen atom, a halogen atom, a lower alkylsulfonyloxy group, a lower alkoxy group or a hydroxyl group;

Z is an oxygen atom, a sulfur atom, a group of the formula

a group of the formula

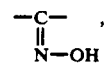

a group of the formula

(wherein $R^3$ is a hydrogen atom or a lower alkyl group) or a group of the formula —NH—;

A is a lower alkylene group;

X is an oxygen atom, a sulfur atom, a group of the formula —SO— or a group of the formula —SO$_2$—;

n is 0 or 1; and the carbon-carbon bond between 3- and 4-positions in the cabrostyril skeleton is a single or double bond.

Said carbostyril derivatives and salts thereof possess activities for inhibiting of thrombocyte adhesion, and thus they can be used as treatment and preventive of arteriosclerosis, ischemic heat disease, chronic arterial obstruction, and an acute or chronic nephritis, as well as they can be used in the treatment of artificial dyalysis and implantation of an artificial organs and the like.

In the present specification, the specific examples of the groups being defined in the respective symbols of R, $R^1$, $R^2$, $R^3$, Z and A are shown below.

The term "a lower alkyl group" means a straight or branched alkyl group having 1 to 6 carbon atoms, and the examples including, methyl, ethyl, propyl, isopropyl, butyl, tert-butyl, pentyl and hexyl groups and the like.

The term "a halo-lower alkyl group" means a straight or branched alkyl group having 1 to 6 carbon atoms having 1 to 3 halogen atoms as the substituents, and the examples including, chloromethyl, bromomethyl, iodomethyl, trifluoromethyl, 2-fluoroethyl, 2,2-difluoroethyl, 2,2,2-trifluoroethyl, 3-chloropropyl, 4-chlorobutyl, 3,4-dichlorobutyl, 3-fluoropentyl, 2,3,4-trifluoropentyl, 2,3-dichlorohexyl and 6,6-dibromohexyl groups and the like.

The term "a halogen atom" means a fluorine atom, a chlorine atom, a bromine atom and an iodine atom.

The term "a lower alkylamino group" means an amino group having 1 or 2 straight or branched alkyl groups having 1 to 6 carbon atoms as the substituents, and the examples including, methylamino, ethylamino, propylamino, tert-butylamino, pentylamino, hexylamino, dimethylamino, diethylamino, di-n-propylamino, di-n-butylamino, dipentylamino, dihexylamino, N-methyl-N-n-butylamino, N-methyl-N-pentylamino and N-ethyl-N-hexylamino groups and the like.

The term "a lower alkoxy group" means a straight or branched alkoxy group having 1 to 6 carbon atoms, and examples including, methoxy, ethoxy, propoxy, isopropoxy, butoxy, tert-butoxy, pentyloxy and hexyloxy groups and the like.

The term "a cycloalkyl group" means a cycloalkyl group having 3 to 8 carbon atoms, and the examples including, cyclopropyl, cyclobutyl, cyclopentyl, cyclohexyl, cycloheptyl and cyclooctyl groups and the like.

The term "a lower alkyl group having 1 or 2 substituents selected from the group consisting of an amino group, a lower alkylamino group and a carboxyl group" means a straight or branched alkyl group having 1 to 6 carbon atoms having 1 to 2 substituents selected from the group consisting of an amino group, a straight or branched alkylamino group having 1 to 6 carbon atoms and a carboxyl group, and the examples including, aminomethyl, 2-methylamino, 1-ethylaminoethyl, 3-propylaminopropyl, 4-tert-butylaminobutyl, 1,1-dimethyl-2-pentylaminoethyl, 5-hexylaminopentyl, 6-dimethylaminohexyl, dimethylaminomethyl, 2-diethylaminoethyl, 1-di-n-propylaminoethyl, 3-di-n-butylaminopropyl, 4-dipentylaminobutyl, 1,1-dimethyl-2-dihexylaminoethyl, 5-(N-methyl-N-n-butylamino)pentyl, 6-(N-methyl-N-pentylamino)hexyl, 2-methyl-3-(N-ethyl-N-hexylamino)propyl, carboxymethyl, 2-carboxyethyl, 1-carboxyethyl, 3-carboxypropyl, 4-carboxybutyl, 1,1-dimethyl-2-carboxyethyl, 5-carboxypentyl, 6-carboxyhexyl, 2-methyl-3-carboxypropyl, 2-amino-2-carboxyethyl, 1-dimethylamino-1-carboxymethyl and 3-amino-2-carboxypropyl groups and the like.

The term "a lower alkoxycarbonyl group" means a straight or branched alkoxycarbonyl group having 1 to 6 carbon atoms, and the examples including, methoxycarbonyl, ethoxycarbonyl, propoxycarbonyl, isopropoxycarbonyl, butoxycarbonyl, pentyloxycarbonyl and hexyloxycarbonyl groups and the like.

The term "a phenyl-lower alkyl group" means a phenylalkyl group in which the alkyl moiety is a straight or branched alkyl group having 1 to 6 carbon atoms, and the examples including, benzyl, 2-phenylethyl, 1-phenylethyl, 3-phenylpropyl, 4-phenylbutyl, 1,1-dimethyl-2-phenylethyl, 5-phenylpentyl and 6-phenylhexyl and 2-methyl-3-phenylpropyl groups and the like.

The term "a lower alkoxy-substituted-phenyllower alkyl group" means a phenylalkyl group in which the alkyl moiety is a straight or branched alkyl group having 1 to 6 carbon atoms, and 1 to 3 straight or branched alkoxy groups having 1 to 6 carbon atoms are substituted on the phenyl ring, and the examples including, 3-methoxybenzyl, 2-(3,4-dimethoxyphenyl)ethyl, 1-(4-ethoxyphenyl)ethyl, 3-(2-propoxyphenyl)propyl, 4-(3-buthoxyphenyl)butyl, 1,1-dimethyl-2-(4-pentyloxyphenyl)ethyl, 5-(4-hexyloxyphenyl)pentyl, 6-(3,4,5-trimethoxyphenyl)hexyl and 2-methyl-3-(2,5-dimethoxyphenyl)propyl groups and the like.

The term "a lower alkylthio group" means a straight or branched alkylthio group having 1 to 6 carbon atoms, and the examples including, methylthio, ethylthio, propylthio, isopropylthio, butylthio, tert-butylthio, pentylthio and hexylthio groups and the like.

The term "a lower alkenyl group" means a straight or branched alkenyl group having 2 to 6 carbon atoms, and the examples including, vinyl, allyl, 2-butenyl, 3-butenyl, 1-methylallyl, 2-pentenyl and 2-hexenyl group and the like.

The term "a phenyl group having 1 to 3 substituents selected from the group consisting of a lower alkyl group, a halo-lower alkyl group, a halogen atom, a hydroxyl group, an amino group, a lower alkylamino group and a lower alkoxy group" means a phenyl group having 1 to 3 substituents selected from the group consisting of a straight of branched alkyl group having 1 to 6 carbon atoms, a straight or branched alkyl group having 1 to 6 carbon atoms having 1 to 3 halogen atoms as the substituents, a halogen atom, a hydroxyl group, an amino group, an amino group having 1 or 2 straight or branched alkyl group having 1 to 6 carbon atoms as the substituents, and a straight or branched alkoxy group having 1 to 6 carbon atoms, and the examples including, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 3,4,5-trimethoxyphenyl, 2,5-dimethoxyphenyl, 3-methyl-4-chlorophenyl, 2-chloro-6-methylphenyl, 2-methoxy-3-chlorophenyl, 2-hydroxyphenyl, 3-hydroxyphenyl, 4-hydroxyphenyl, 3,4-dihydroxyphenyl, 3,4,5-trihydroxyphenyl, 2-aminophenyl, 3-aminophenyl, 4-aminophenyl, 2,4-diaminophenyl, 2-methylaminophenyl, 3-methylaminophenyl, 4-methylaminophenyl, 2-ethylaminophenyl, 3-ethylaminophenyl, 4-ethylaminophenyl, 4-isopropylaminophenyl, 4-hexylaminophenyl, 3,4-dimethylaminophenyl, 2-(dimethylamino)phenyl, 3-(dimethylamino)phenyl, 4-(dimethylamino)phenyl, 2-(diethylamino)phenyl, 3-(N-methyl-N-ethylamino)phenyl, 4-(N-methyl-N-isopropylamino)phenyl, 4-(N-isopropyl-N-hexylamino)phenyl, 2-(di-n-butylamino)phenyl, 2-trifluoromethylphenyl, 3-(3-chloropropyl)phenyl, 4-(2-fluoroethyl)phenyl, 2-(4-chlorobutyl)phenyl, 3-(3-bromopentyl)phenyl, 2-(iodomethyl)phenyl, 4-(2,3-dichlorohexyl)- phenyl, and 3-(2,2,2-trifluoroethyl)phenyl groups and the like.

The term "an unsaturated heterocyclic residual group having 1 to 5 hetero atoms selected from the group consisting of a nitrogen atom, an oxygen atom and a sulfur atom" including, 1,2,4-triazolyl, imidazolyl, 1,2,3,5-tetrazolyl, 1,2,3,4-tetrazolyl, pyrrolyl, benzimidazolyl, 1,3,4-triazolyl, imidazolynyl, pyridyl, pyrimidinyl, pyrazolyl, pyrazolinyl, thiazolyl, thiazolinyl, 1,3,4-oxadiazolyl, 1,3,4-thiadiazolyl, thienyl, furyl, pyranyl, isothiazolyl, isooxazolyl, pyrazinyl, pyridazinyl, indolyl, isoindolyl, 3H-indolyl, indolizinyl, indazolyl, quinolyl, isoquinolyl, phthalazinyl, naphthyridinyl, quinoxalinyl, quinazolinyl, cinnolinyl, pyrrolinyl, pyrazolinyl, indolinyl and isoindolinyl groups and the like can be exemplified.

The term "said unsaturated heterocyclic residual group which may have 1 to 3 substituents, on the heterocyclic residual ring, selected from the group consisting of an oxo group; a thio group; a phenyl group; a phenyl group having 1 to 3 substituents, on the phenyl ring, selected from the group consisting of a lower alkyl group, a halo-lower alkyl group, a halogen atom, a hydroxyl group, an amino group, a lower alkylamino group, a carboxy group and a lower alkoxy group; a cycloalkyl group; a phenylthio group; a lower alkyl group; a lower alkyl group having 1 to 2 substituents selected from the group consisting of an amino group, a lower alkylamino group and a carboxyl group; an amino group; a hydroxyl group; a cyano group; a carboxyl group; a lower alkoxycarbonyl group; a phenyl-lower alkyl group which may have hydroxyl groups as the substituents on the phenyl ring; a phenylsulfonyl group which may have lower alkyl groups as the substituents on the phenyl ring; a lower alkoxy-substituted phenyl-lower alkyl group; a lower alkylthio group; a lower alkenyl group; a lower alkoxy group and a pyridyl group" means an unsaturated heterocyclic residual group which may have 1 to 3 substituents, on the heterocyclic residual ring, selected from the group consisting of an oxo group; a thio group; a phenyl group; a phenyl group having 1 to 3 substituents, on the phenyl ring, selected from the group consisting of the above-mentioned lower alkyl group, the above-mentioned halo-lower alkyl group, the above-mentioned halogen atom, a hydroxyl group, an amino group, the above-mentioned lower alkylamino group, a carboxy group and the above-mentioned lower alkoxy group; the above-mentioned cycloalkyl group; a phenylthio group; the above-mentioned lower alkyl group; the above-mentioned lower alkyl group having 1 to 2 substituents selected from the group consisting of an amino group, the above-mentioned lower alkylamino group and a carboxyl group; an amino group; a hydroxyl group; a cyano group; a carboxyl group; the above-mentioned lower alkoxycarbonyl group; the above-mentioned phenyl-lower alkyl group which may have hydroxyl groups as the substituents on the phenyl ring; the above-mentioned phenylsulfonyl group which may have lower alkyl groups as the substituents on the phenyl ring, the above-mentioned lower alkoxy-substituted phenyl-lower alkyl group; the above-mentioned lower alkylthio group; the above-mentioned lower alkenyl group; the above-mentioned lower alkoxy group and a pyridyl group, and the examples including, 2-phenylthiopyrrolyl, 2-methylimidazolyl, 2-ethylimidazolyl, 2-propylimidazolyl, 4-n-butylimidazolyl, 4-pentylimidazolyl, 4-hexylimidazolyl, 2-phenylimidazolyl, 2-phenylthioimidazolyl, 2-phenylthio-1,3,5-triazolyl, 3-phenylthio-1,2,4-triazolyl, 1-phenylimidazolyl, 1-ethylimidazolyl, 5-methylimidazolyl, 5-methoxybenzimidazolyl, 1-ethylbenzimidazolyl, 6-ethoxybenzimidazolyl, 7-propoxybenzimidazolyl, 4-n-butoxybenzimidazolyl, 5-pentyloxybenzimidazolyl, 6-hexyloxybenzimidazolyl, 1-phenyl-1,3,4-triazolyl, 1-phenyl-1,2,3,4-tetrazolyl, 1-(3-pyridyl)imidazolyl, 1-(2-methylphenyl)imidazolyl, 1-(2-methoxyphenyl)imidazolyl, 1-(4-methylphenyl)imidazolyl, 1-(3-ethylphenyl)imidazolyl, 1-4-propylphenyl)imidazolyl, 1-(2-n-butylphenyl)imidazolyl, 1-(3-pentylphenyl)imidazolyl, 1-(4-hexylphenyl)imidazolyl, 1-(3-ethoxyphenyl)imidazolyl, 1-(4-methoxyphenyl)imidazolyl, 1-(4-propoxyphenyl)imidazolyl, 1-(2-n-butoxyphenyl)imidazolyl, 1-(3-pentyloxyphenyl)imidazolyl, 1-(4hexyloxyphenyl)imidazolyl, 1-allylimidazolyl, 1-(2butenyl)imidazolyl, 1-(3-butenyl)imidazolyl, 1-(1methylallyl)imidazolyl, 1-(2-pentenyl)imidazolyl, 1-(2hexenyl)imidazolyl, 1-benzylimidazolyl, 1-(2-phenylethyl)imidazolyl, 1-(1-phenylethyl)imidazolyl, 1-(3-phenylpropyl)imidazolyl, 1-(4-phenylbutyl)imidazolyl, 1-(6-phenylhexyl)imidazolyl, 1-(5-phenylpentyl)imidazolyl, 1-ethyl-1,3,4-triazolyl, 4-ethyl-1,3,4-triazolyl, 1-methyl-1,3,4-triazolyl, 4-propyl-1,3,4-triazolyl, 1-benzyl-1,3,4-triazolyl, 4-benzyl-1,3,4-triazolyl, 1-(2-phenylethyl)-1,3,4-triazolyl, 3-methylpyrazolyl, 4-ethylpyrazolyl, 3-propylpyrazolyl, 3-n-butylpyrazolyl, 1-ethylpyrrolyl, 1-methylpyrrolyl, 1-propylpyrrolyl, 1-n-butylpyrrolyl, 1-allylbenzimidazolyl, 1-(2-butenyl)benzimidazolyl, 1-(3-butenyl)benzimidazolyl, 1-(1-methylallyl)benzimidazolyl, 1-(2-pentenyl)benzimidazolyl, 1-(2-hexenyl)benzimidazolyl, 1-(2-trifluoromethylphenyl)imidazolyl, phenyl)imidazolyl, 1-(4-hydroxyphenyl)imidazolyl, 1-(4-dimethylaminophenyl)imidazolyl, 1-(3,4-difluorophenyl)imidazolyl, 1-(3,4,5-trichlorophenyl) imidazolyl, 1-[4-(2-fluoroethyl)phenyl]imidazolyl, 1-[4-(2,3-dichlorohexyl)phenyl]imidazolyl, 1-[3-(3-chloropropyl)phenyl] imidazolyl, 1-(2-aminophenyl)imidazolyl, 1-(2-ethylaminophenyl)imidazolyl, 1-(4-isopropylaminophenyl) imidazolyl, 1-[4-(N-methyl-N-hexylamino)phenyl]imidazolyl, 2-cyclopropyl-1,3,4-oxadiazolyl, 2-cyclohexyl-1,3,4-oxadiazolyl, 2-cycloheptyl-1,3,4-oxadiazolyl, 2-cycloctyl-1,3,4-oxadiazolyl, 1-cyclohexylimidazolyl, 1-cyclopentyl-1,3,4-triazolyl, 1-cyclopropylbenzimidazolyl, 2-methylthioimidazolyl, 4-ethylthioimidazolyl, 2-propylthioimidazolyl, 4-n-butyrylthioimidazolyl, 4-pentylthioimidazolyl, 2-hexylthioimidazolyl, 1-ethyl-5,6-dimethoxy-benzimidazolyl, 2-phenyl-3,4-dimethylpyrrolyl, 1,2,3-trimethylimidazolyl, 2,4,5-trichloropyridyl, 3,4,5-trimethoxypyridyl, 2-(2-amino-2-carboxyethyl)imidazolyl, 2-methyl-3-dimethylaminomethylimidazolyl, 2-carboxymethyl-3-methylimidazolyl, 3-methyl-5-pyrazolinyl, 3-methyl-4-hydroxypyrazolyl, 4-amino-5-cyanoimidazolyl, 4-methyl-5-ethoxycarbonylimidazolyl, 4-methyl-5-carboxyimidazolyl, 1-[2-(3,4-dihydrophenyl)ethyl]-1,2,3,4-tetrazolyl, 1-(3-pyridyl)-5-thio-1,2,3,4-tetrazolyl, 1-phenyl-5-1,2,3,4-tetrazolyl, 1-(4-phenylsulfonyl)pyrrolyl and 1-(4-carboxyphenyl)imidazolyl groups and the like.

The term "a lower alkylene group" mean a straight or branched alkylene group having 1 to 6 carbon atoms, and the examples including, methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene groups and the like.

The term "a phenyl-lower alkyl group which may have hydroxyl groups as the substituents on the phenyl ring" means a phenyl alkyl group in which the alkyl moiety is a straight of branched alkyl group having 1 to 6 carbon atoms, and the phenyl ring may have 1 to 3 hydroxyl group as the substituents, and the examples including, in addition to the above-mentioned phenyl-lower alkyl group, 3-hydroxybenzyl, 2-(3,4-dihydroxyphenyl)ethyl, 1-(4-hydroxyphenyl)ethyl, 3-(2-hydroxyphenyl)propyl, 4-(3-hydroxyphenyl)butyl, 1,1-dimethyl-2-(4-hydroxyphenyl)ethyl, 5-(4-hydroxyphenyl)pentyl, 6-(3,4,5-trihydroxyphenyl)hexyl and 2-methyl-3-(2,5-dihydroxyphenyl)propyl groups and the like.

The term "a phenylsulfonyl group which may have lower alkyl groups as the substituents on the phenyl ring" means a phenylsulfonyl group which may have 1 to 3 straight or branched alkyl groups having 1 to 6 carbon atoms as the substituents on the phenyl ring, and the examples including, phenylsulfonyl, 2-methylphenylsulfonyl, 3-methylphenylsulfonyl, 4-methylphenylsulfonyl, 2-ethylphenylsulfonyl, 3-isopropylphenylsulfonyl, 4-hexylphenylsulfonyl, 2-pentylphenylsulfonyl, 3,4-dimethylphenylsulfonyl, 2,5-dimethylphenylsulfonyl and 3,4,5-trimethylphenylsulfonyl groups and the like.

The term "a lower alkylsulfonyloxy group" means a straight or branched alkylsulfonyloxy group having 1 to 6 carbon atoms, and the examples including, methylsulfonyloxy, ethylsulfonyloxy, propylsulfonyloxy, isopropylsulfonyloxy, butylsulfonyloxy, tert-butylsulfonyloxy, pentylsulfonyloxy and hexylsulfonyloxy groups and the like.

The side-chain of the formula —Z—A—(X)n—R may be substituted any one of 3-, 4-, 5-, 6-, 7- or 8-position in the carbostyril skeleton.

Carbostyril derivative and salts thereof represented by the general formula (1) according to the present invention can be prepared by various methods, and preferable methods can be exemplified by reaction process formulas as follows.

Reaction process formula - 1

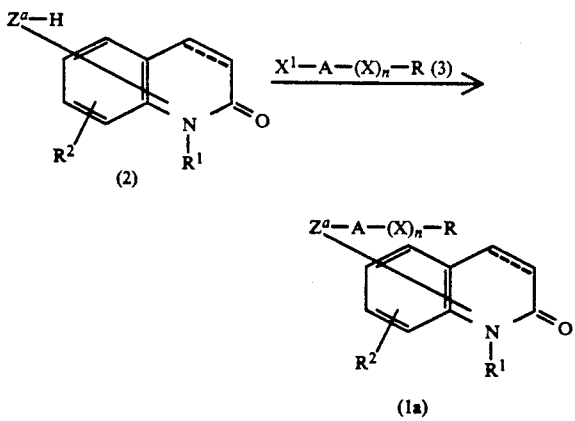

(wherein R, R$^1$, R$^2$, A, X, n and the carbon-carbon bond between 3- and 4-positions in the carbostyril skeleton are the same as defined above; Z$^a$ is an oxygen atom, a sulfur atom or a group of —NH—; and X$^l$ is a halogen atom a lower alkanesulfonyloxy group, an arylsulfonyloxy group or an aralkylsulfonyloxy group).

Among the substituents represented by the symbol X$^l$, as to the lower alkanesulfonyloxy group, the examples including, methanesulfonyloxy, ethanesulfonyloxy, propanesulfonyloxy, isopropanesulfonyloxy, butanesulfonyloxy, tert-butanesulfonyloxy, pentanesulfonyloxy and hexanesulfonyloxy groups and the like; as to the arylsulfonyloxy group, the examples including, phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy and α-naphthylsulfonyloxy groups and the like; further as to the aralkylsulfonyloxy group, the examples including, benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 4-chlorobenzylsulfonyloxy and α-naphthylsulfonyloxy groups and the like.

The reaction of a compound of the general formula (2) with a compound of the general formula (3) can be carried out in a suitable solvent or without solvent, in the presence of a basic compound. As to the basic compound, any known basic compound can be selected from a wide range, and the examples including, inorganic basic compounds such as sodium hydroxide, potassium hydroxide, sodium carbonate, sodium hydrogen carbonate, potassium hydrogen carbonate and silver carbonate and the like; alkali metals such as sodium metal, potassium metal and the like; alcoholates such as sodium methylate, sodium ethylate and the like; organic basic compounds such as triethylamine, pyridine, N,N-dimethylamine, N-methylmorpholine, 4-dimethylaminopyridine, 1,5-diazabicyclo[4.3.0]nonene (DBN), 1,8-diazabicyclo[5.4.0]undecene-7 (DBU) and 1,4-diazabicyclo[2.2.2]octane (DABCO) and the like. As to the solvent, any inert solvent which does not give any adverse effect to the reaction can be used, and the examples alcohols such as methanol, ethanol, propanol, butanol and ethylene glycol and the like; ethers such as dimethyl ether, tetrahydrofuran, dioxane, ethylene glycol dimethyl ether and diethylene glycol dimethyl ether and the like; ketones such as acetone, methyl ethyl ketone and the like; aromatic hydrocarbons such as benzene, toluene and xylene and the like; esters such as methyl acetate, ethyl acetate and the like; aprotic polar solvents such as N,N-dimethylformamide (DMF), dimethyl sulfoxide (DMSO), hexamethylphosphoric triamide (HMPA) and the like. The reaction can also be carried out in the presence of a metal iodide such as sodium iodide, potassium iodide or the like.

Ratio of the amount of a compound of the general formula (2) to the amount of a compound of the general formula (3) is not specifically restricted, and it can be selected from a wide range, and generally an equimolar quantity to 5 times the molar quantity, preferably an equimolar quantity to 2 times the molar quantity of the latter may be used to the former. Temperature of the above-mentioned reaction is not specifically restricted, and generally the reaction can be carried out at about room temperature to 200° C., preferably at about 50° to 150° C., and completes generally in about 5 minutes to 30 hours.

Reaction process formula - 2

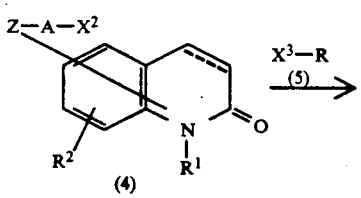

(wherein R, R¹, R², Z, A and the carbon-carbon bond between 3- and 4-positions in the carbostyril skeleton are the same as defined above; X² and X³ are each is the same as defined in X¹, or a group of the formula —Y—H wherein Y is an oxygen atom or a sulfur atom; provided that, when X² is the same as defined in X¹, then X³ is a group of the formula —Y—H; alternatively, when X² is a group of the formula —Y—H, then X³ is the same as defined in X¹).

The reaction of a compound of the general formula (4) with a compound of the general formula (5) can be carried out under the reaction conditions similar to those employed in the reaction of a compound of the general formula (2) with a compound of the general formula (3) as in the Reaction process formula - 1.

Reaction process formula - 3

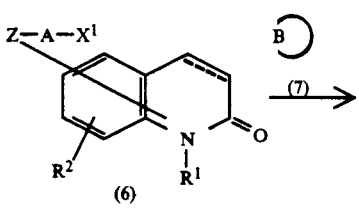

(wherein R¹, R², Z, A, X¹ and the carbon-carbon bond between 3- and 4-positions in the carbostyril skeleton are the same as defined above;

are each is a unsaturated heterocyclic residual group having 1 to 4 nitrogen atoms, oxygen atoms or sulfur atoms; provided that said heterocyclic residual group should have at least one nitrogen atom; further said heterocyclic ring may have 1 to 3 substituents selected from the group consisting of an oxo group; a thio group; a phenyl group; a phenyl group which may have 1 to 3 substituents, on the phenyl ring, selected from the group consisting of a lower alkyl group, a halo-lower alkyl group, a halogen atom, a hydroxyl group, an amino group, a lower alkylamino group, a carboxy group and a lower alkoxy group; a cycloalkyl group; a phenylthio group; a lower alkyl group; a lower alkyl group having 1 to 2 substituents selected from the group consisting of an amino group, a lower alkylamino group and a carboxyl group; an amino group; a hydroxyl group; a cyano group; a carboxyl group; a lower alkoxycarbonyl group; a phenyl-lower alkyl group which may have hydroxyl groups as the substituents on the phenyl ring; a phenylsulfonyl group which may have lower alkyl groups as the substituents on the phenyl ring; a lower alkoxy-substituted phenyl-lower alkyl group; a lower alkylthio group; a lower alkenyl group; a lower alkoxy group and a pyridyl group; the above-mentioned group of

is a group of a group of

or a group of

and the above-mentioned B$^a$ is a group of

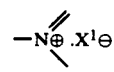

or a group of

The reaction of a compound of the general formula (6) with a compound of the general formula (7) can be carried out in the presence or absence of a basic compound, preferably in the presence of a basic compound in a suitable solvent. As to the basic compound, any known basic compound can be selected from a wide range and can be used, for example metal hydroxides such as sodium hydroxide, potassium hydroxide and the like; alkali metal alcoholates such as sodium methylate, sodium ethylate, potassium methylate, potassium ethylate and the like; alkali metal amides such as sodium amide, potassium amide and the like; alkali metals such as sodium metal, potassium metal and the like; alkali metal hydride such as sodium hydride, potassium hydride and the like; and DBU can be exemplified.

The amount of the basic compound is not specifically restricted, and can be selected from a wide range, generally an equimolar quantity to a large excess quantity, preferably 1 to 3 times the molar quantity of the basic compound may be used to a compound of the general formula (6). As to the solvent, any common inert solvent can be selected from a wide range and used, examples including, lower alcohols such as methanol, ethanol, isopropanol and the like; ethers such as diethyl ether, tetrahydrofuran, dioxane and the like; ketones such as acetone, methyl ethyl ketone, cyclohexane, acetophenone and the like; aromatic hydrocarbons such as benzene, toluene, xylene and the like; esters such as methyl acetate, ethyl acetate and the like; polar solvents such as dimethylformamide, hexanethylphosphoric triamide, acetonitrile and the like. The reaction can also be carried out in the presence of a metal iodide such as sodium iodide, potassium iodide or the like. Ratio of the amount of a compound of the general formula (6) to the amount of a compound of the general formula (7) is not specifically restricted and can be selected from a wide range, and generally an equimolar quantity to a large excess quantity, preferably 1 to 2 times the molar quantity of the latter may be used to the former. The reaction can be proceeds generally at 0° C. to about 200° C., preferably from room temperature to about 150° C., and the reaction completes in 10 minutes to about 24 hours.

In the above-mentioned reaction, when a compound of the general formula (6) in which Z is a group of the formula

is used, a compound of the formula (6) is first reacted with a dihydroxy-lower alkylene such as ethylene glycol or propylene glycol to convert Z into a group of the formula

(wherein W is a lower alkylene group) so as to protected, then said protected compound of the general formula (6) is reacted with a compound of the general formula (7), then the protecting group in the protected group is removed to obtain a compound of the general formula (1c) in which Z is a group of the formula

The above-mentioned protecting reaction can be carried out in the presence of an acid in a suitable solvent. As to the acid used in this protecting reaction, mineral acids such as hydrochloric acid, hydrobromic acid, sulfuric acid and the like, organic acid such as p-toluenesulfonic acid, pyridine p-toluenesulfonate, acetic acid, propionic acid and the like can be exemplified. As to the solvent, lower alcohols such as methano, ethanol, isopropanol and the like; ethers such as diethyl ether, tetrahydrofuran, dioxane and the like; ketones such as acetone and the like; aromatic hydrocarbons such as benzene, toluene, xylene and the like, aliphatic hydrocarbons such as n-hexane, n-octane and the like; alkane acids such as acetic acid, propionic acid and the like; acetonitrile or mixed solvents thereof can be exemplified.

Ratio of the amount of dihydroxy-lower alkylene to the amount of a compound of the general formula (6) may be generally at least an equimolar quantity, preferably in about 1 to 5 times the molar quantity of the former to the latter. The reaction is generally carried out at 0° to about 150° C., preferably at 0° to 100° C., and completes in about 0.5 to 10 hours.

Removal reaction of the protecting group is carried out in the presence of an acid in the presence or absence of a suitable solvent. As to the acid used in this removal reaction, any acid as mentioned above can be used. The amount of the acid is at least an equimolar quantity, preferably a large excess quantity of the acid may be used to the starting material. As to solvent, water, dimethylformamide and dimethyl sulfoxide may be exemplified in addition to the solvents mentioned above. The reaction is generally proceeded at -30 to 200° C., and preferably at about −30° to 100° C., and completes in about 0.5 to 12 hours.

Reaction process formula - 4

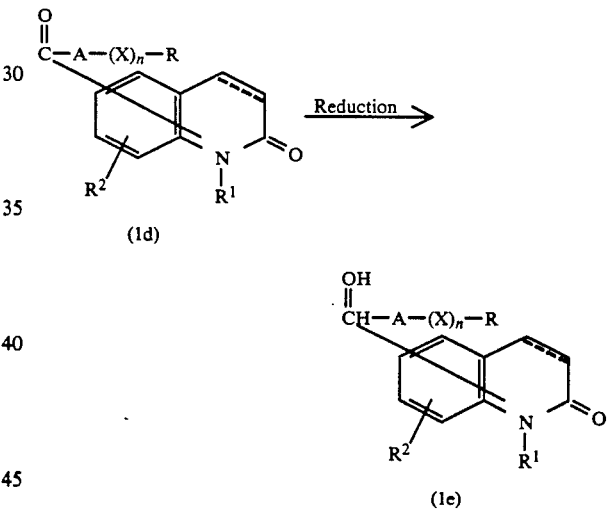

(wherein R, R¹, R², A, X, n and the carbon-carbon bond between 3- and 4-positions in the carbostyril skeleton are the same as defined above).

The reduction of a compound of the general formula (1d) can be carried out by a reducing method using a hydrogenating reducing agent, or catalytic reducing method.

In case of carrying out the reducing method by using a hydrogenating reducing agent, sodium borohydride, lithium aluminum hydride or the like, preferably sodium borohydride can be used as the hydrogenating reducing agent. The hydrogenating reducing agent may be used generally in an amount at least an equimolar quantity, preferably 1 to 3 times the molar quantity thereof to a compound of the general formula (1d). The hydrogenating reduction is carried out in a solvent, for example water, a lower alcohol such as methanol, ethanol, isopropanol or the like; an ether such as tetrahydrofuran, diethyl ether or the like; dimethylformamide or the like; or a mixed solvent thereof, and at about −60° to 100° C., preferably at about −30° to 70° C., and the reaction complete in 10 minutes to 3 hours. In case of using lithium aluminum hydride as the reducing agent, an anhydrous solvent, such as diethyl ether, tetrahydrofuran or the like may be used as the solvent.

In case of employing catalytic reducing method, platinum oxide, palladium black, palladium-carbon, Raney-nickel or the like can be used as the reducing catalyst. The amount of the catalyst may be generally 0.2 to 0.5 times the part by weight to a compound of the general formula (1d). The catalytic reducing method is carried out in a solvent for example, water; a lower alcohol such as methanol, ethanol, isopropanol or the like; an ether such as tetrahydrofuran, diethyl ether or the like, and under 1 to 10 atmospheric pressure, preferably under 1 to 3 atmospheric pressure of hydrogen atmosphere with a sufficient shaking condition. The catalytic reduction is carried out generally at $-30°$ C. to the boiling point of the solvent, preferably at $0°$ C. to about room temperature.

Reaction process formula - 5

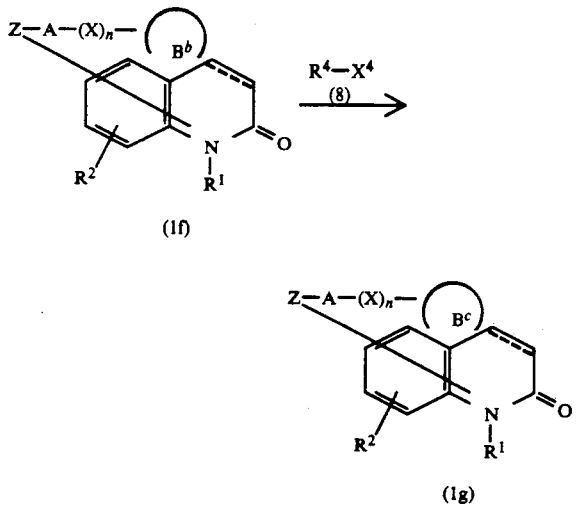

(wherein $R^1$, $R^2$, Z, A, X, n and the carbon-carbon bond between 3- and 4-positions in the carbostyril skeleton are the same as defined above; and $X^4$ is a halogen atom; groups of the formulas

are each an unsaturated heterocyclic residual group having 1 to 4 nitrogen atoms, oxygen atoms or sulfur atoms, provided that said heterocyclic residual group should contain at least one nitrogen atom; further, said unsaturated heterocyclic residual group may have 1 to 3 substituents, on the heterocyclic ring, selected from the group consisting of an oxo group, a thio group; a phenyl group; a phenyl group which may have 1 to 3 substituents, on the phenyl ring, selected from the group consisting of a lower alkyl group, a halo-lower alkyl group, a halogen atom, a hydroxy group, an amino group, a lower alkylamino group, a carboxy group and a lower alkoxy group; a cycloalkyl group; a phenylthio group; a lower alkyl group; a lower alkyl group having 1 to 2 substituents selected from the group consisting of an amino group, a lower alkylamino group and a carboxyl group; an amino group; a hydroxyl group; a cyano group; a carboxyl group; a lower alkoxycarbonyl group; a phenyl-lower alkyl group which may have hydroxyl groups as the substituents on the phenyl ring; a phenylsulfonyl group which may have lower alkyl groups as the substituents on the phenyl ring; a lower alkoxy-substituted phenyl-lower alkyl group; a lower alkylthio group; a lower alkenyl group; a lower alkoxy group and a pyridyl group; above-mentioned group of the formula —$B^b$— is —NH—; and group of the formula —$B^c$— is

((wherein $R^4$ is a phenyl group; a phenyl group having 1 to 3 substituents, on the phenyl ring, selected from the group consisting of a lower alkyl group, a halo-lower alkyl group, a halogen atom, a hydroxy group, an amino group, a lower alkylamino group, a carboxy group and a lower alkoxy group; a cycloalkyl group; a phenylthio group; a lower alkyl group; a phenyl-lower alkyl group which may have hydroxyl groups as the substituents on the phenyl ring; a phenylsulfonyl group which may have lower alkyl groups as the substituents on the phenyl ring; a lower alkenyl group; a lower alkyl group which may have 1 to 2 substituents selected from the group consisting of a lower alkylamino group and a carboxylgroup; a lower alkoxycarbonyl group; a lower alkoxy-substituted phenyl-lower alkyl group and a pyridyl group))).

The reaction of a compound of the general formula (1f) with a compound of the general formula (8) can be carried out in the presence of a basic substance, in a suitable solvent. As to the basic substance, examples including, sodium hydride, potassium metal, sodium metal, sodium amide, potassium amide, sodium hydroxide, potassium hydroxide and the like. As to the solvent, examples including, ethers such as dioxane, diethylene glycol dimethyl ether and the like; aromatic hydrocarbons such as toluene, xylene and the like; polar solvents such as dimethylformamide, dimethyl sulfoxide, hexamethylphosphoric triamide and the like. The reaction may also be carried out, if necessary, by adding a copper halide such as copper iodide; metal iodide such as sodium iodide, potassium iodide and the like; copper powder and the like to the reaction system.

Ratio of the amount of a compound of the general formula (1f) to the amount of a compound of the general formula (8) is not specifically restricted, and can be selected from a wide range, generally at least an equimolar quantity, preferably 1 to 3 times the molar quantity of the latter may be used to the former. The reaction is generally proceeded at $0°$ to $100°$ C., preferably at about $0°$ to $70°$ C., and completes in 5 minutes to 12 hours.

Reaction process formula - 6

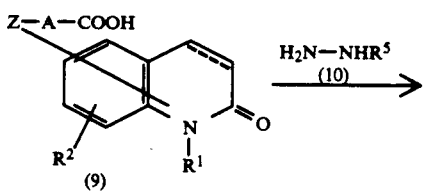

-continued

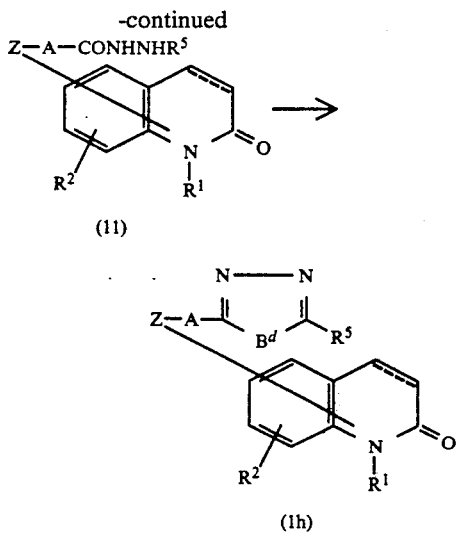

(wherein $R^1$, $R^2$, Z, A and the carbon-carbon bond between 3- and 4-positions in the carbostyril skeleton are the same as defined above; $R^5$ is a group of the formula —$COR^6$ or a group of the formula —$CSR^6$ ((wherein $R^6$ is a phenyl group; a phenyl group which may have 1 to 3 substituents, on the phenyl ring, selected from the group consisting of a lower alkyl group, a halo-lower alkyl group, a halogen atom, a hydroxyl group, an amino group, a lower alkylamino group, a carboxy group and a lower alkoxy group; a cycloalkyl group; a phenylthio group; a lower alkyl group; a lower alkyl group having 1 to 2 substituents selected from the group consisting of an amino group, a lower alkylamino group and a carboxyl group; an amino group; a cyano group; a carboxyl group; a lower alkoxycarbonyl group; a phenyl-lower alkyl group which may have hydroxyl groups as the substituents on the phenyl ring; a phenylsulfonyl group which may have lower alkyl groups as the substituents on the phenyl ring; a lower alkoxy-substituted phenyl-lower alkyl group; a lower alkylthio group; a lower alkenyl group; a lower alkoxy group and a pyridyl group)); and $B^d$ is an oxygen atom or a sulfur atom).

The reaction of a compound of the general formula (9) with a compound of the general formula (10) can be easily carried out under conditions similar to those known in amino-bond formation reactions. In the present invention, the reaction can be carried out by using a compound in which the carboxyl group being activated, in place of a compound of the general formula (9). As to typical methods are, for example, (a) mixed acid anhydride method: by reacting a carboxylic acid (9) with an alkylhalocarboxylic acid to form the corresponding mixed acid anhydride, then reacting said mixed acid anhydride with a hydrazine derivative (10); (b) activated ester method: by converting a carboxylic acid (9) into the corresponding activated ester thereof, such as p-nitrophenyl ester, N-hydroxysuccinimide ester, 1-hydroxybenzotriazol ester or the like, then reacting said activated ester of carboxylic acid (9) with a hydrazine derivative (10); (c) carbodiimide method: by condensing a carboxylic acid (9) with a hydrazine derivative (10) in the presence of an activating agent, such as dicyclohexylcarbodiimide, carbonyldiimidazol or the like; (d) other methods: by reacting a carboxylic acid (9) with a dehydrating agent such as acetic anhydride to prepare the corresponding carboxylic anhydride, then reacting said carboxylic acid anhydride with a hydrazine derivative (10); by reacting a carboxylic acid (9) with a lower alcohol to form the ester, then reacting said ester with a hydrazine derivative (10) under a high pressure at a high temperature; by reacting an acid halide of a carboxylic acid (9), i.e., a carboxylic halide with a hydrazine derivative (10). Among the above-mentioned methods, the mixed acid anhydride method is the most preferable.

In carrying out the mixed acid anhydride method, as to the alkylhalocarboxylic acid used in the reaction, examples including methyl chloroformate, methyl bromoformate, ethyl chloroformate, ethyl bromoformate, isobutyl chloroformate and the like. Said mixed acid anhydride can be obtained generally by Schotten-Baumann reaction, generally said mixed acid anhydride is reacted with a hydrazine derivative (10), without separated from the reaction system, to obtain a compound of the general formula (11).

Schotten-Baumann reaction is carried out in the presence of a basic compound. As to the basic compound, any basic compound used in Schotten-Baumann reaction can be used, the examples including, organic basic compounds such as triethylamine, trimethylamine, pyridine, dimethylaniline, N-methylmorpholine, 1,5-diazabicyclo-[4.3.0]nonene-5 (DBN), 1,8-diazabicyclo[5.4.0]undecene-7 (DBU), 1,4-diazabicyclo[2.2.2]octane (DABCO) and the like; and inorganic basic compounds such as potassium carbonate, sodium carbonate, potassium hydrogen carbonate, sodium hydrogen carbonate and the like. The Schotten-Baumann reaction is carried out generally at −20° to 100° C., preferably at 0° to 50° C., and completes generally in about 5 minutes to 10 hours.

The reaction of the mixed acid anhydride thusobtained above with a compound (10) is generally carried out in a solvent. As to the solvent used in the reaction, any usual solvent employed in mixed acid anhydride method can also be used, and the examples including, halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; aprotic polar solvents such as dimethylformamide, dimethyl sulfoxide, hexamethylphosphoric triamide and the like. The reaction is generally carried out at −20° to 150° C., preferably at 10° to 50° C., and completes generally in about 5 minutes to 10 hours.

Ratio of the amount of a compound (9) to the amount of the alkylhalocarboxylic acid and a compound (10) in the above-mentioned reaction is generally an equimolar quantity each of these compounds, and there may be used 1 to 1.5 times the molar quantity of the alkylhalocarboxylic acid and the compound (10) may be used to the compound (9).

The reaction for obtaining a compound of the general formula (1h) by ring-closing a compound of the general formula (11) can be carried out according to various methods known in usual ring-closing reactions. For example, method by heating, ring-closing methods by using dehydrating agents such as phosphorus oxychloride, phosphorus pentachloride, phosphorus trichloride, acetyl chloride, p-toluenesulfonic acid, benzenesulfonic acid, thionyl chloride, concentrated sulfuric acid, hydrochloric acid, acetic anhydride, polyphosphoric acid and the like. In carrying out a method by heating, the reaction is carried out by using a high boiling point-hydrocarbon or a high boiling point ether, as the solvent, and the examples including tetrahydronaphthalene, diphenyl ether, dethylene glycol dimethyl ether, decaline, tetraline, toluene, xylene, mesitylene, chlorobenzene, bromobenzene and the like, and the reaction can be carried out under heating conditions at about 100° to 250° C., preferably, at about 150° to 200° C. In carrying out ring-closing method by using a dehydrating agent, the use of polyphosphoric acid as the dehydrating agent is the most desirable. Said polyphosphoric acid is generally used in an equimolar quantity to a large excess quantity, preferably 10 to 20 times of the quantity may be used to the compound (11), and the reaction is generally carried out at about 100° to 250° C., and completes, generally in about 5 minutes to 6 hours.

In the above-mentioned Reaction process formula - 6, a compound (9) being used as the starting material is a known compound, and compounds (10) contain partially known compounds and including some novel compounds. Such novel compounds can be prepared by method similar to those employed in the preparation of known compounds, for example they can be prepared by method of the following Reaction process formula - 7.

Reaction process formula - 7

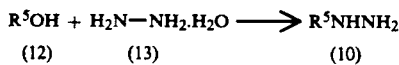

(wherein $R^5$ is the same as defined above).

The reaction of a compound of the general formula (12) with a compound of the general formula (13) can be carried out by methods similar to those employed in the reaction of a compound (9) with a compound (10).

Reaction process formula - 8

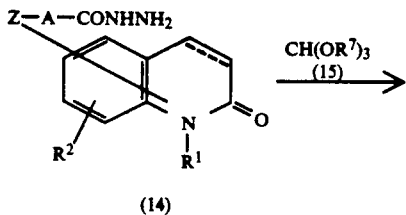

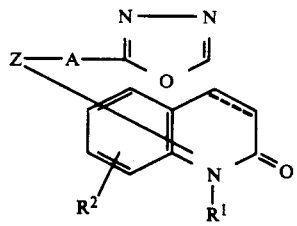

(wherein $R^1$, $R^2$, Z, A and the carbon-carbon bond between 3- and 4-positions in the carbostyril skeleton are the same as defined above; and $R^7$ is a lower alkyl group).

The reaction of a compound of the general formula (14) with a compound of the general formula (15) is carried out in the absence or presence of a suitable solvent. As to the solvent used in the reaction, the examples including, high boiling point solvents, for example, aromatic hydrocarbons such as benzene, toluene, xylene or the like; ethers such as dimethoxyethane, diphenyl ether, dioxane or the like.

Ratio of the amount of the compound (14) to the amount of the compound (15) may be generally an equimolar quantity to a large excess quantity, preferably 2 to 50 times the molar quantity of the latter to the former. The reaction is carried out, generally at 50° to 250° C., preferably at 80° to 200° C., and completes generally in about 1 to 40 hours.

Reaction process formula - 9

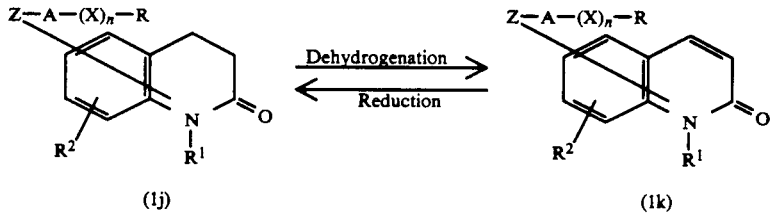

(wherein R, $R^1$, $R^2$, Z, A, X and n are the same as defined above).

The dehydrogenation of a compound of the general formula (1j) is carried out, by a conventional method, in a suitable solvent by using an oxidizing agent. As to the oxidizing agent, the examples including, benzoquinones such as 2,3-dichloro-5,6-dicyanobenzoquinone (DDQ), chloranil (2,3,5,6-tetrachlorobenzoquinone) and the like; selenium dioxide; metal catalysts such as palladium-carbon and the like; brominating agents such as N-bromosuccinimide, bromine and the like. As to amount of the oxidizing agent, in case of using a benzoquinone or a brominating agent, generally an equimolar to 5 times the molar quantity, preferably an equimolar to 2 times the molar quantity of the oxidizing agent may be used to a compound of the general formula (1j). As to the solvent used in the reaction, the examples including, ethers such as dioxanem tetrahydrofuran, 2-methoxyethanol, dimethoxyethane and the like; aromatic hydrocarbons such as benzene, toluene, xylene and the like; halogenated hydrocarbons such as dichloromethane, dichloroethane, chloroform, carbon tetrachloride and the like; alcohols such as butanol, amyl alcohol, hexanol and the like; aprotic polar solvents such as dimethylformamide, dimethyl sulfoxide, hexamethylphosphoric triamide or the like. The reaction is carried out generally at room temperature to 300° C., preferably at about 50° to 200° C., and completes, generally in about 1 to 48 hours.

The catalytic reduction of a compound of the general formula (1k) is carried out by conventional method, in a suitable solvent in the presence of a catalyst by hydrogenation. As to the catalyst used in the hydrogenation, any known catalyst may be selected and used, the examples including, platinum catalysts such as platinum wire, platinum plate, platinum sponge, platinum black, platinum oxide, colloidal platinum and the like; palladium catalysts such as palladium sponge, palladium black, palladium oxide, palladium-barium sulfate, palladium-barium carbonate, palladium-carbon, palladium-silica gel, colloidal palladium and the like; platinum group catalysts such as asbestos with rhodium, iridium, colloidal rhodium, ruthenium catalyst, colloidal iridium and the like; nickel catalysts such as reduced nickel, nickel oxide, Raney-nickel, Urushibara-nickel, nickel catalyst formed by thermal decomposition of nickel formate, nickel boride and the like; cobalt catalysts such as reduced cobalt, Raney cobalt, Urushibara cobalt and the like; iron catalysts such as reduced iron, Raney iron and the like; reduced copper, Raney copper, Ullmann copper and the like; and other metallic catalysts such as zinc and the like. As to the solvents, the examples including, lower alcohol such as methanol, ethanol, isopropanol and the like; water; acetic acid; acetate esters such as methyl acetate, ethyl acetate and the like; ethers such as ethylene glycol diethyl ether, diethyl ether, tetrahydrofuran, dioxane and the like; aromatic hydrocarbons such as benzene, toluene, xylene and the like; cycloalkanes such as cyclopentane, cyclohexane and the like; n-alkanes such as n-hexane, n-pentane and the like.

The above reaction can be carried out generally under atmospheric pressure or pressurized hydrogen atmosph atmosphere, and preferably at 1 to 20 atmospheric pressure, and the reaction is generally proceeds at room temperature to the boiling temperature of the solvent used, preferably at room temperature to 100° C.

Reaction process formula - 10

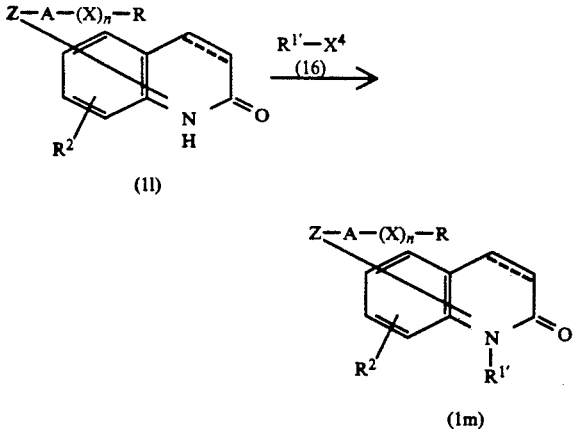

(wherein R, R², Z, A, X, n, X⁴ and the carbon-carbon bond between 3- and 4-positions in the carbostyril skeleton are the same as defined above; and R¹' is a lower alkyl group or a phenyl-lower alkyl group).

The reaction of a compound of the general formula (11) with a compound of the general formula (16) can be carried out under conditions similar to those employed in the reaction of compound (1f) with compound (8) in the above-mentioned Reaction process formula - 5.

In this reaction, among compounds represented by the general formula (11) in which the heterocyclic residual group as indicated by the symbol R having a group of —NH— in said heterocyclic residual group may be reacted with a compound represented by the general formula (16), however the resulting product can be separated easily from the desired compound represented by the general formula (1m).

Reaction process formula - 11

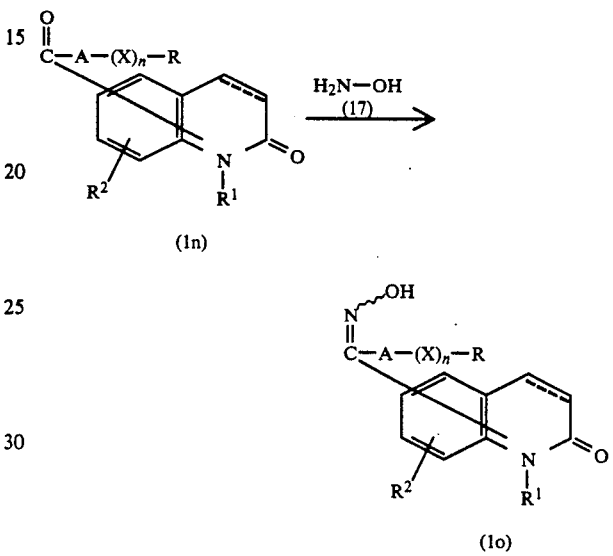

(wherein R, R¹, R², A, X, n and the carbon-carbon bond between 3- and 4-positions in the carbostyril skeleton are the same as defined above).

The reaction of a compound represented by the general formula (1n) with hydroxylamine (17) can be carried out in a suitable solvent, and in the presence or absence of a basic compound. As to the basic compound used in the reaction, the examples including, inorganic basic compounds such as sodium hydroxide, potassium hydroxide, sodium carbonate, potassium carbonate and the like; organic basic compounds such as piperidine, pyridine, triethylamine, 1,5-diazabicyclo[4.3.0]nonene-5 (DBN), 1,8-diazabicyclo[5.4.0]undecene-7 (DBU), 1,4-diazabicyclo[2.2.2.]octane (DABCO) and the like. As to the solvent used in the reaction, water; alcohols such as methanol, ethanol, isopropanol and the like; ethers such as dioxane, tetrahydrofuran, diethyl ether, ethylene glycol dimethyl ether and the like; aromatic hydrocarbons such as benzene, toluene, xylene and the like; halogenated hydrocarbons such as dichloremethane, dichloroethane, chloroform, carbon tetrachloride and the like; polar solvents such as dimethylformamide (DMF), dimethyl sulfoxide (DMSO), hexamethylphosphoric triamide (HMPA) and the like.

Ratio of the amount of compound (1n) with hydroxylamine (17) may be generally at least an equimolar quantity, preferably 1 to 5 times the molar quantity of the latter to the former. The reaction is generally carried out at 0° to 150° C., preferably at 0° to 100° C., and generally completes in 10 minutes to 10 hours.

Reaction process formula - 12

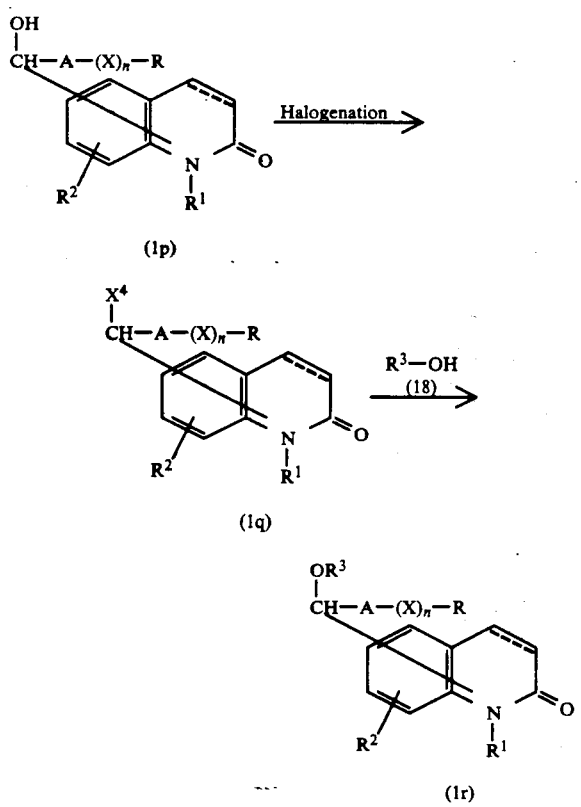

(wherein R. $R^1$, $R^2$, $R^3$, A, X, n, $X^4$ and the carbon-carbon bond between 3- and 4-positions in the carbostyril skeleton are the same as defined above).

The halogenation of a compound of the general formula (1p) is carried out in the presence of a halogenating agent, and in the absence or presence of a suitable solvent. As to the halogenating agent, the examples including, hydrohalogenic acids such as hydrochloric acid, hydrobromic acid and the like; N,N-diethyl-1,2,2-trichlorovinylamide, phosphorus pentachloride, phosphorus pentabromide, phosphorus oxychloride, thionyl chloride.

The halogenating agent may be used at least an equimolar quantity, generally in a large excess quantity to a compound of the general formula (1p). As to the solvent, the examples including, ethers such as dioxane, tetrahydrofuran, diethyl ether and the like; halogenated hydrocarbons such as chloroform, methylene chloride, carbon tetrachloride and the like. The halogenation is carried out generally at −20° to 150° C., preferably at −20° to 80° C., and completes in about 10 minutes to 6 hours.

The reaction of a compound of the general formula (1q) with a compound of the general formula (18) can be carried out in the absence or presence of a basic compound, in a suitable solvent or without the solvent. As to the basic compound used in the reaction, the examples including, inorganic basic compounds such as sodium hydroxide, potassium hydroxide, sodium carbonate, potassium carbonate, sodium hydrogen carbonate, potassium hydrogen carbonate, sodium amide, sodium hydride and the like; alcoholates such as sodium methylate, sodium ethylate and the like; and organic basic compounds such as triethylamine, pyridine, N,N-dimethylaniline and the like. As to the solvents used in the reaction, water; lower alcohols such as methanol, ethanol, isopropanol, and the like; halogenated hydrocarbons such as dichloromethane, dichloroethane, chloroform, carbon tetrachloride and the like; ethers such as diethyl ether, tetrahydrofuran, dioxane and the like; aliphatic hydrocarbons such as n-hexane, octane, cyclohexane and the like; aromatic hydrocarbons such as benzene, toluene, xylene and the like; polar solvents such as acetone, acetonitrile, dimethylformamide (DMF), dimethyl sulfoxide (DMSO), hexamethylphosphoric triamide (HMPA) and the like, and mixed solvents thereof. Ratio of the amount of a compound (1q) to the amount of a compound (18) may be at least an equimolar quantity, generally a large excess quantity of the latter to the former. The reaction is generally proceeds at 0° to 150° C., preferably at 0°to 100° C., and completes in about 10 minutes to 10 hours.

Reaction process formula - 13

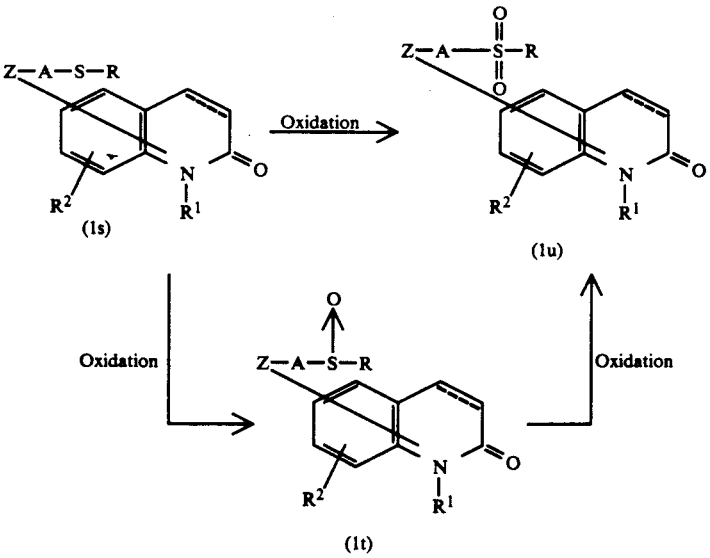

(wherein R, $R^1$, $R^2$, Z, A and the carbon-carbon bond between 3- and 4-positions in the carbostyril skeleton are the same as defined above).

The reaction for obtaining a compound of the general formula (1t) by oxidizing a compound of the general formula (1s), the reaction for preparing a compound of the general formula (1u) by oxidizing a compound of the general formula (1s), and the reaction for obtaining a compound of the general formula (1u) by oxidizing a compound of the general formula (1t) can be carried out in the presence of a oxidizing agent in a suitable solvent. As to the oxidizing agent used in these reactions, any known oxidizing agent for obtaining sulfoxide group or sulfone group by oxidizing sulfide group can be used, the examples including, peracids such as performic acid, peracetic acid, pertrifluoroacetic acid, perbenzoic acid, m-chloroperbenzoic acid, o-carboxylperbenzoic acid and the like; hydrogen peroxide; bichromic acid; bichromates such as sodium bichromate, potassium bichromate and the like; permanganic acid; permangantes such as sodium permanganate, potassium permanganate and the like. As to the solvents, the examples including, water, organic acids such as formic acid, acetic acid, trifluoroacetic acid and the like; alcohols such as methanol, ethanol and the like; halogenated hydrocarbons such as chloroform, dichloromethane and the like; and mixed solvents thereof.

The above-mentioned reaction is proceeded generally at $-20°$ to $40°$ C., preferably at about $-20$ to room temperature, and the reaction completes generally in about 0.5 to 50 hours.

In case of to obtain compound (1t) by oxidizing compound (1s), generally at least an equimolar quantity, preferably 1 to 1.5 times the molar quantity of the oxidizing agent may be used to compound (1s). In case of to obtain compound (1u) by oxidizing compound (1s), generally at least 2 times the molar quantity, preferably 2 to 4 times the molar quantity of the oxidizing agent may be used to compound (1s). In case of to obtain comp compound (1u) by oxidizing compound (1t), generally at least an equimolar quantity, preferably 1 to 4 times the molar quantity of the oxidizing agent may be used to compound (1t).

Reaction process formula - 14

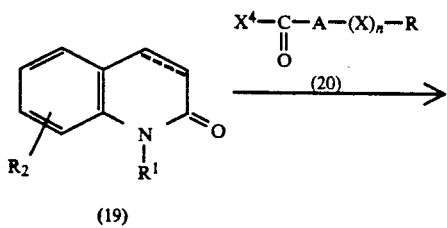

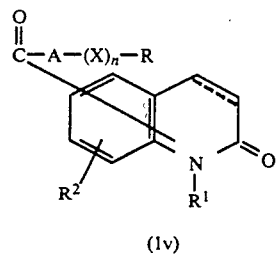

(wherein R, $R^1$, $R^2$, A, X, n, X4 and the carbon-carbon bond between 3- and 4-positions in the carbostyril skeleton are the same as defined above).

The reaction of a compound of the general formula (19) with a compound of the general formula (20) is called generally as Friedel-Crafts reaction, can be carried out in the presence of a Lewis acid, in a suitable solvent. As to the Lewis acid used in this reaction, the examples including, aluminum chloride, zinc chloride, ferric chloride, stannic chloride, boron tribromide, boron trifluoride, concentrated sulfuric acid and the like. The amount of the Lewis acid used in this reaction is generally an equimolar quantity of 6 times the molar quantity, preferably 1 to 4 times the molar quantity to a compound of the general formula (19). As to the solvent used in the reaction, the examples including, carbon disulfide; aromatic hydrocarbons such as nitrobenzene, chlorobenzene and the like; halogenated hydrocarbons such as dichloromethane, dichloroethane, chloroform, carbon tetrachloride, trichloroethane, tetrachloroethane and the like. Ratio of trichloroethane, tetrachloroethane and the like. Ratio of the amount of compound (19) to the amount of compound (20) may be generally at least an equimolar quantity, preferably 1 to 4 times the molar quantity of the latter to the former. The reaction generally proceeds at $0°$ to $120°$ C., preferably at about $0°$ to $70°$ C., and completes generally in 0.5 to 6 hours.

Compound of the general formula (6) which is used as the starting material in the above-mentioned Reaction process formula - 3, and compound of the general formula (9) which is used as the starting material in the above-mentioned Reaction process formula - 6 can be prepared by the methods respectively shown in the following Reaction process formula -15 and -16.

Reaction process formula - 15

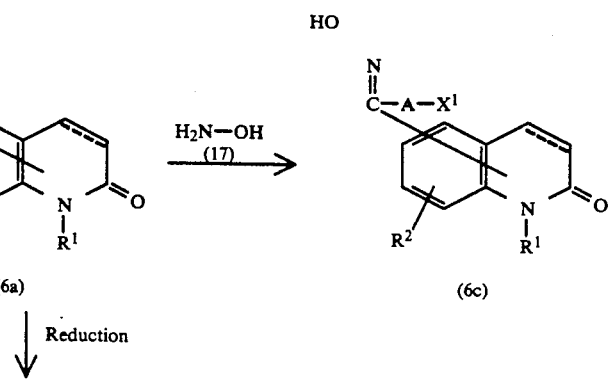

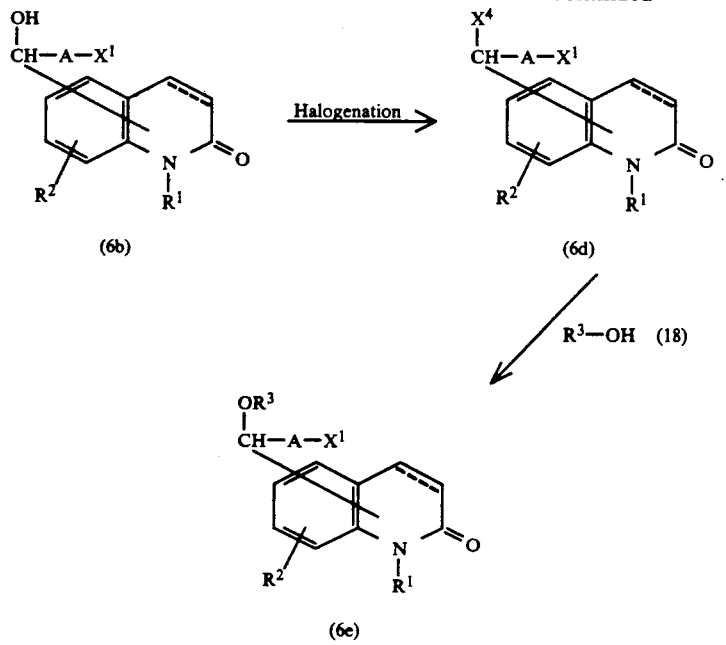

(wherein R, $R^1$, $R^2$, $R^3$, A, $X^1$, $X^4$ and the carbon-carbon bond between 3- and 4-positions in the carbostyril skeleton are the same as defined above).

The reduction of a compound of the general formula (6a) can be carried out under the conditions similar to those employed in the reduction of a compound of the general formula (1d) in Reaction process formula - 4.

The halogenation of a compound of the general formula (6b) can be carried out under conditions similar to those employed in the halogenation of a compound of (1p) in Reaction process formula - 12.

The reaction of a compound of the general formula (6d) with a compound of the general formula (18) can be carried out under conditions similar to those employed in the reaction of a compound (1q) with a compound of the general formula (18) in Reaction process formula (12). In this reaction, compound of the general formula (6d) in which $X^1$ is substituted with a group of the formula —$OR^3$, and also compound of the general formula (6d) in which each of $X^1$ and $X^4$ is substituted with a group of the formula —$OR^3$ may be formed, and these products can be easily separated from the desired compound of the general formula (6e).

The reaction of compound of the general formula (6a) with hydroxylamine (17) can be carried out under conditions similar to those employed in the reaction of compound (1n) with hydroxylamine (17) in Reaction process formula - 11. In this reaction, compound of the general formula (6a) in which $X^1$ is reacted with hydroxylamine (17) may be formuld, and such compound can easily be separated from the desired product of the general formula (6c).

Reaction process formula - 16

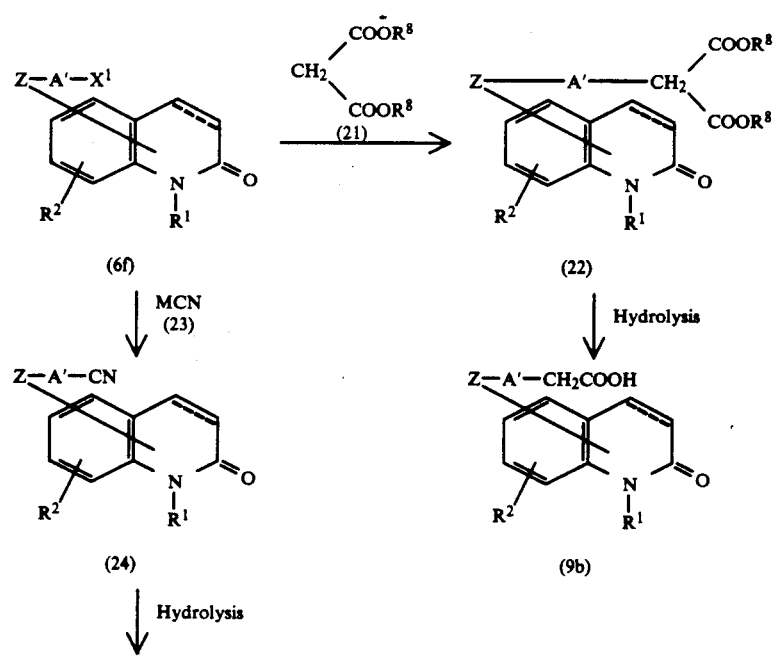

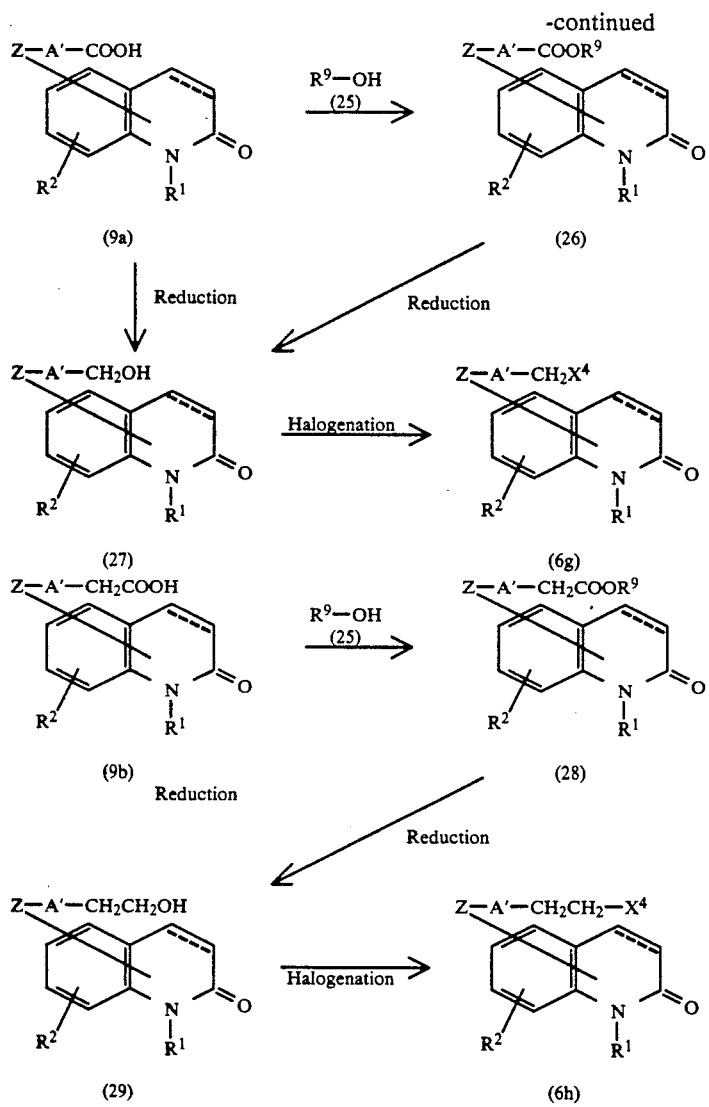

(wherein $R^1$, $R^2$, Z, $X^1$, $X^4$ and the carbon-carbon bond between 3- and 4-positions in the carbostyril skeleton are the same as defined above; $R^8$ and $R^9$ are each a lower alkyl group; and A' is a lower alkylene group).

The reaction of a compound of the general formula (6f) with a compound of the general formula (23) is carried out in a suitable solvent. As to the compound of the general formula (23), the examples including cyanides such as potassium cyanide, sodium cyanide, silver cyanide, copper cyanide, calcium cyanide and the like. As to the solvent, the examples including water; alcohols such as methanol, ethanol, isopropanol and the like; and mixed solvents thereof.

Ratio of the amount of compound (1f) to the amount of compound (23) may be at least an equimolar quantity, preferably 1 to 1.5 times the molar quantity of of the latter to the former. The reaction is carried out at room temperature to 150° C., preferably at about 50° to 120° C., and completes generally in 30 minutes to 10 hours.

The hydrolysis of compound of the general formula (24) is carried out in the presence of a hydrolysis catalyst, the examples including, mineral acids for example hydrohalogenic acids such as hydrochloric acid, hydrobromic acid and the like; sulfuric acid; phosphoric acid and the like; alkali metal hydroxides such as sodium hydroxide, potassium hydroxide and the like; alkali metal carbonates and hydrogen carbonates such as sodium carbonate, potassium carbonate, sodium hydrogen carbonate and the like, and in the absence or presence of a suitable solvent. As to the solvent used in the hydrolysis, the examples including, water, alcohols such as methanol, ethanol and the like and mixtures of these solvents. The hydrolysis is carried out generally at 50° to 150° C., preferably at about 70° to 100° C., and completes generally in 1 to 24 hours, and thus compound of the general formula (9a) can be obtained.

The reaction of a compound of the general formula (6f) with a compound of the general formula (21) can be carried out in the presence of a basic compound, in a suitable solvent. As to the basic compound used in the reaction, the examples including, inorganic basic compounds such as calcium carbonate, sodium carbonate, potassium carbonate, sodium hydrogen carbonate, sodium hydroxide, potassium hydroxide, sodium amide, sodium hydride, potassium hydride, sodium methylate, sodium ethylate and the like; amines such as triethylamine, tripropylamine, pyridine, quinoline and the like. As to the solvent used in the reaction, ethers such as dioxane, tetrahydrofuran, ethylene glycol dimethyl ether, diethyl ether and the like; aromatic hydrocarbons such as benzene, toluene, xylene and the like; lower alcohols such as methanol, ethanol, isopropanol and the like; polar solvents such as dimethylformamide (DMF), dimethyl sulfoxide (DMSO), and the like. The reaction can advantageously be proceeded in the presence of an alkali metal iodide, the examples including, potassium iodide, sodium iodide and the like in the reaction system.

Ratio of the amount of compound (6f) to the amount of compound (19) may be generally be in an equimolar quantity to a large excess quantity, preferably 1 to 5 times the molar quantity, more preferably 1 to 1.2 times the molar quantity of the latter to the former. The reaction is carried out generally at room temperature to 200° C., preferably at about 60° to 120° C., and completes in 1 to 24 hours.

The hydrolysis of a compound of the general formula (22) can be carried out under conditions similar to those employed in the hydrolysis of a compound of the general formula (24), thus a compound of the general formula (9b) can be obtained.

The reaction of a compound of the general formula (9a) or a compound of the general formula (9b) with a compound of the general formula (25) can be carried out under conditions similar to those employed in a usual esterification reaction, for example, method (1) by reacting in a suitable solvent in the presence of a dehydrating agent; and method (2) by reacting in a suitable solvent in the presence of an acid or a basic compounds and the like.

In carrying out the above-mentioned method (1), as to the solvents, the examples including, halogenated hydrocarbons such as dichloromethane, chloroform, dichloroethane, carbon tetrachloride and the like; aromatic hydrocarbons such as benzene, toluene, xylene and the like; ethers such as diethyl ether, tetrahydrofuran, dioxane, ethylene glycol momomethyl ether, dimethoxyethane and the like; polar solvents such as dimethylformamide (DMF), dimethyl sulfoxide (DMSO), hexamethylphosphoric triamide (HMPA) and the like. As to the dehydrating agent, the examples including, dicyclohexylcarbodiimide, carbonyldiimidazol and the like. An amount of the dehydrating agent used in this reaction may be generally at least an equimolar quantity, preferably 1 to 1.5 times the molar quantity to a compound (9a) or (9b). Ratio of the amount of compound (9a) or (9b) to the amount of compound (25) may be generally at least an equimolar quantity, preferably 1 to 1.5 times the molar quantity of the latter to the former. The reaction can be carried out generally at room temperature to 150° C., preferably at about 50° to 100° C., and completed generally in 1 to 10 hours.

In carrying out the above-mentioned method (2), as to the acid used in the reaction, the examples including, inorganic acids such as hydrogen chloride, sulfuric acid, phosphoric acid, polyphosphoric acid, boron trifluoride, perchloric acid and the like; organic acids such as trifluoroacetic acid, trifluoromethanesulfonic acid, naphthalenesulfonic acid, p-toluenesulfonic acid, benzenesulfonic acid, ethanesulfonic acid and the like; acid anhydrides such as trichloromethanesulfonic anhydride, trifluoromethanesulfonic anhydride and the like; thionyl chloride; acetonedimethylacetal and the like. Further, acidic ion-exchange resins can also be used. As to the basic compounds, inorganic basic compounds such as sodium hydroxide, potassium hydroxide, sodium carbonate, potassium carbonate, sodium hydrogen carbonate, potassium hydrogen carbonate, silver carbonate and the like; alcoholates such as sodium methylate, sodium ethylate and the like. This reaction can be carried out in the absence of a solvent, while the reaction can advantageously be carried out in the solvent as mentioned in the above-mentioned method (1). Further, the reaction can advantageously be carried out by using a drying agent such as, anhydrous calcium chloride, anhydrous copper sulfate, anhydrous calcium sulfate, phosphorus pentoxide or the like.

An amount of compound of the general formula (25) may be a large excess quantity when the reaction is carried out in the absence of the solvent, while, when the reaction is carried out in the presence of the solvent, it may be used generally at least an equimolar to 5 times the molar quantity, preferably generally 1 to 2 times the molar quantity. The reaction can be carried out generally at $-20°$ to 200° C., preferably at about 0° to 150° C., and completes generally in 1 to 20 hours. The reduction of compound (9a), compound (9b), compound (26) or compound (28) can be carried out in a suitable solvent, in the presence of a hydrogenating reducing agent. As to the reducing agent, the examples including, sodium borohydride, lithium aluminum hydride, diborane and the like. An amount of the reducing agent may be at least an equimolar quantity, preferably 1 to 3 times the molar quantity to the compound to be treated. Particularly, in case of using lithium aluminum hydride as the reducing agent, an equivalent part by weight of the reducing agent may preferably be used to the compound to be treated. As to the solvent used in the reaction, the examples including, water, lower alcohols such as methanol, ethanol and isopropanol and the like; ethers such as tetrahydrofuran, diethyl ether, diethylene glycol dimethyl ether and the like. The reaction can be generally carried out at $-60°$ to 50° C., preferably at about $-30°$ C. to room temperature, and completes generally in 10 minutes to 5 hours.

The halogenation of a compound of the general formula (27) or a compound of the general formula (29) can be carried out under conditions similar to those employed in the halogenation of a compound of the general formula (1p).

By repeating the above-mentioned Reaction process formula - 16, a compound of the general formula (6) or (9) can be prepared.

Carbostyril derivatives represented by the general formula (1) can be converted into salts form by reacting with a pharmaceutically acceptable acid. As to the acid, the examples including, inorganic acids such as hydrochloric acid, hydrobromic acid, sulfuric acid, phosphoric acid and the like; organic acid such as oxalic acid, succinic acid, maleic acid, fumaric acid, acetic acid, malic acid, citric acid, lactic acid and the like.

Among carbostyril derivatives represented by the general formula (1), those having acidic groups can be converted into salt form by reacting with a pharmaceutically acceptable basic compound, the examples including, alkali metals and alkaline earth metals hydroxides such as sodium hydroxidem potassium hydroxide, calcium hydroxide and the like.

Compounds according to the present invention inevitably contain their optical isomers.

Carbostyril derivatives and salts thereof represented by the general formula (1) according to the present invention can be used in any form of usual pharmaceutical compositions which are prepared by using usual pharmaceutically acceptable carriers. Examples of such pharmaceutically acceptable carriers are selected depending on the desired form of pharmaceutical compositions including diluents and excepients such as fillers, diluents, binders, wetting agents, disintegrating agents, surface active agents, lubricants, and the like. The pharmaceutical compositions can be selected from any desired form depending on the purpose of therapy, including tablets, pills, powders, liquors, suspensions, emulsions, granules, capsules, supositories, injection preparations (e.g., solutions and suspensions, and thers), etc.

For the purpose of to prepare tablet form compositions, carriers which are widely used in this field can be used, for example, excipients such as lactose, sucrose, sodium chloride, gluocose, urea, starch, calcium carbonate, kaolin, crystalline cellulose, silicic acid, etc.; binding agents such as water, ethanol, propanol, simple syrup, glucose solutions, starch solutions, gelatin solutions, carboxymethyl cellulose, shelac, methyl cellulose, calcium phosphate, polyvinylpyrrolidone, etc.; disintegrating agents such as dried starch, sodium alginate, agar-agar powder, laminalia power, sodium hydrogen carbonate, calcium carbonate, esters of polyoxyethylene sorbitan fatty acids, monoglyceride of stearic acid, starch, lactose, etc.; disintegration inhibitors such as sucrose, stearin, coconut butter, hydrogenated oils, etc.; absorption accelerators such as quaternary ammonium bases, sodium laurylsulfonate, etc.; wetting agents such as glycerin, starch, etc.; adsorbing agents such as lactose, kaolin, bentonite, colloidal silicic acid, etc.; and lubricants such as purified talc, stearic acid salts, boric acid powder, polyethylene glycols, etc. if necessary, the tablets can further be coated with usual coating materials to make the tablets into the form of coated tablets, for example, tablets coated with sugar, tablets coated with gelatin film, tablets coated with enteric coating layers, tablets coated with films or double layered tablets and multi-layered tablets.

For the purpose f to shape in the form of pills, carriers which are known and widely used in this field can also be used, for example, excipients such as glucose, lactose, starch, coconut butter, hydrogenated vegetable oils, kaolin and talc; binders such as powdered Gummi Arabicum, powdered tragacanth, gelatin and ethanol; disintegrators, such as laminaria and agar-agar are included.

For the purpose of to shape in the form of suppositories, carriers, which are known and widely used in this field can also be used, for example, polyethylene glycols, coconut butter, higher alcohols, esters of higher alcohols, gelatin and semi-synthesized glycerides are included.

For the purpose of to make in the form of injection preparations, solutions and suspensions are sterilized and are preferably isotonic to blood. In making injection preparations in the form of solutions, emulsions and suspensions, every diluents which are commonly used in this field can also be used, for example, water, aqueous solution of lactose, ethyl alcohol, propylene glycol, ethoxylated isostearyl alcohol, polyoxylated isostearyl alcohol and polyoxyethylene sorbitan fatty acid esters are included. In these instances, an adequate amount of sodium chloride, glucose or glycerin can be added to contain in the desired preparations for the purpose of to have them isotonic. Furthermore, usual dissolving agents, buffers, analgesic agents and other agents can be added, as well as coloring agents, preservatives, perfumes, seasoning agents, sweetning agents and other medicines can also be added into the desired preparations, if necessary.

For the purpose of to make in the form of pastes, creams and gels, white petrolatum, paraffin, glycerin, cellulose derivatives, polyethylene glycols, silicones, bentonite can be used as the diluents.

Amount of compound of the general formula (1) or salt thereof to be contained in the pharmaceutical compositions according to the present invention is not specifically restricted and can suitably be selected from wide range, and generally, 1 to 70% by weight of the whole composition is used.

Method for administering the pharmaceutical compositions according to the present invention are not specifically restricted, and the compositions can be used in various forms of preparations depending upon the age, the distinction of gender, the degree of symptoms and other conditions of the patient without any restriction. For example, tablets, pills, solutions, suspensions, emulsions, granules and capsules are administered orally; injection preparations are administered intraveneously singly, or administered with usual injectable transfusions such as glucose solutions, amino acid solutions and others; if necessary the injection preparations are administered singly intramuscularly, intracutaneously, subcutaneously or intraperitoneally. The suppositories are administered into rectum.

The dosage of carbostyril derivative or salt thereof represented by the general formula (1) according to the present invention can be selected suitably depend pm the method for administrations, the age of the patient, the distinction of gender and other conditions, as well as a degree of the symptoms, and generally a pharmaceutical composition containing a carbostyril derivative or salt thereof represented by the general formula (1), as the active ingredient, in an amount of 0.06 to 100 mg/kg of the body weight per day may used. Such pharmaceutical composition can be administered 2 to 4 times a day, separately.

The present invention will be illustrated more in detail bh referring to Examples of Pharmaceutical Preparations, Pharmacological Test Results, Reference Examples and Examples, however, the present invention are not restricted only by those disclosures.

Preparation of Pharmaceutical Compositions (1) Preparation of Tablets

| Formulation | |
|---|---|
| 6-[2-(1-Phenyl-2-imidazolyl)thioacetyl]-3,4-dihydrocarbostyril | 5 g |
| Lactose (Japanese Pharmacopoeia) | 50 g |
| Corn starch (Japanese Pharmacopoeia) | 25 g |
| Crystalline cellulose (Japanese Pharmacopoeia) | 25 g |
| Methylcellulose (Japanese Pharmacopoeia) | 1.5 g |
| Magnesium stearate (Japanese Pharmacopoeia) | 1.0 g |

By using an usual procedure, 1,000 tablets having the above-mentioned formulation were prepared by admixing 6-[2-(1-phenyl-2-imidazolyl)thioacetyl]-3,4-dihydrocarbostyril, lactose, corn starch and crystalline cellulose throughly, then the mixture was shaped in granular by adding 55-methylcellulose aqueous solution, and the granules were passed through a 200 mesh sieve and dried carefully. The dried granules were shaped as in the form of tablets by usual procedure.

(2) Preparation of capsules

| Formulation | |
|---|---|
| 6-3-[1-(3-Pyridyl)-2-imidazolyl)-thiopropoxy]-3,4-dihydrocarbostyril | 10 g |
| Lactose (Japanese Pharmacopoeis) | 80 g |
| Starch (Japanese Pharmacopoeia) | 30 g |
| Talc (Japanese Pharmacopoeia) | 5 g |
| Magnesium stearate (Japanese Pharmacopoeia) | 1 g |

Each of the above-mentioned ingredients were ground finely to make them uniform mixture by agitating thoroughly, then the mixture was filled in a capsule having desired size for oral administration. 1,000 Capsules filled with the mixture were prepared.

(3) Preparation of injection solution

| Formulation | |
|---|---|
| 6-[2-(1-Phenyl-2-imidazolyl)thioacetyl]-3,4-dihydrocarbostyril | 1 g |
| Polyethylene glycol (M.W. 4,000) (Japanese Pharmacopoeia) | 0.3 g |
| Sodium chloride (Japanese Pharmacopoeia) | 0.9 g |
| Polyoxyethylene sorbitan monooleate (Japanese Pharmacopoeia) | 0.4 g |
| Sodium metabisulfite | 0.1 g |
| Methyl p-hydroxybenzoate (Japanese Pharmacopoeia) | 0.18 g |
| Propyl p-hydroxybenzoate (Japanese Pharmacopoeia) | 0.02 g |
| Distilled water for injection | 100 (ml) |

The above-mentioned methyl p-hydroxybenzoate, propyl p-hydroxybenzoate, sodium metabisulfite and sodium chloride were dissolved in a half volume of the distilled water for injection at 80° C. with stirring. Thus obtained solution was cooled to 40° C., then 6-[2-(1-phenyl-2-imidazolyl)thioacetyl]-3,4-dihydrocarbostyril, polyethylene glycol and polyoxyethylene sorbitan monooleate were dissolved therein. Then the remaining volume of the distilled water was added to the solution so as to adjust the final volume of the injection solution. Thus prepared solution was sterilized by a suitable filter paper, then the sterilized solution was filled in an ampule to prepare the desired injection preparation.

Pharmacological Test (1) Test method

Activities for inhibiting of thrombocyte adhesion performed by carbostyril derivative and salt thereof represented by the general formula (1) were determined by "Salzman glass beads method".

Each of test compounds was suspended in 1%-gum arabi aqueous solution, and orally administered to Wister strain male rate (weighing 150–200 g) in the rate of 100 mg/kg/5 ml. 3 Hours after the administration, the rate was anesthetized with ether and laparotomized, then the blood was sampled, in the rate of 1 ml/min, from the abdominal descending aorta, by using an apparatus for fixed-time sampling of blood (manufactured by Igaku-Shoin Kikai Sha), through a column packed with glass-beads (manufactured by Igaku-Shoin Kikai Sha). Similar to rats in the test group, rats in the control group were orally administered 1%-gum arabi aqueous solution without containing test compound, and the blood was also sampled.

The sample of blood was then instantaneously transferred into a plastic bottle (Model Sysmex SB-41, manufactured by Toa Iyoh-Denshi Sha) containing EDTA, and the sample of blood was mixed rotationally by using a rolling mixer (manufactured by Thermal Scientific Co., Ltd.). The number of thrombocytes in the blood sample was counted by using an automatic blood corpuscule conter (Model ELT-8, manufactured by Orthodiagnostic Co.). The thrombocytes adhesion rate (%) was calculated from the following formula, $$\text{Thrombocytes adhesion rate (\%)} = \frac{A - B}{A} \times 100$$

wherein

A: the number of thrombocytes in blood passed through the reference column, without packed with glass-beads.

B: the number of thrombocytes in blood passed through the test column packed with glass-beads.

Thrombocytes adhesion inhibitory rate (%) was calculated from the following formula.

$$\text{Thrombocytes adhesion inhibitory rate (\%)} = \frac{C - D}{C} \times 100$$

wherein

C: thrombocytes adhesion rate (%) of control group

D: thrombocytes adhesion rate (%) of test group.

Test results are shown in the following Table 1.

(2) Test compounds

| Test compound No. | |
|---|---|
| 1. | 6-[3-(1-Methyl-1,2,3,4-tetrazol-5-yl)-thiopropoxy]-3,4-dihydrocarbostyril |
| 2. | 6-[3-(2-Cyclohexyl-1,3,4-oxadiazol-5-yl)-propoxy]-3,4-dihydrocarbostyril |
| 3. | 6-[3-(1-Imidazolyl)propoxy]carbostyril hydrochloride |
| 4. | 6-[3-(2-Cyclohexyl-1,3,4-oxadiazol-5-yl)-propoxy]carbostyril |
| 5. | 6-[3-(1,2,4-Triazol-1-yl)propoxy]-3,4-dihydrocarbostyril |
| 6. | 6-[3-(1,2,3,4-Tetrazol-1-yl)propoxy]-3,4-dihydrocarbostyril |
| 7. | 6-[3-(2-Methyl-1-imidazolyl)propoxy]-3,4-dihydrocarbostyril |
| 8. | 6-[3-(1,2,4-Triazol-1-yl)propoxy]carbostyril |
| 9. | 6-[3-(2-Methyl-1-imidazolyl)propoxy]carbostyril |
| 10. | 6-[3-(1,2,4,5-Tetrazol-1-yl)propoxy]carbostyril |
| 11. | 6-[3-(1,2,3,4-Tetrazol-1-yl)propoxy]carbostyril |
| 12. | 6-[3-(1-Phenyl-2-imidazolyl)thiopropoxy]-3,4-dihydrocarbostyril |
| 13. | 6-[3-(1-Imidazolyl)propoxy]-3,4-dihydrocarbostyril |
| 14. | 6-[3-(1-Phenyl-1,3,4-triazol-2-yl)thiopropoxy]-3,4-dihydrocarbostyril |
| 15. | 6-[3-(2-Imidazolyl)thiopropoxy]-3,4-dihydrocarbostyril |
| 16. | 6-[3-(1-Ethyl-2-imidazolyl)thiopropoxy]-3,4-dihydrocarbostyril |
| 17. | 8-[3-(1,2,4-Triazol-1-yl)propoxy]-3,4-dihydrocarbostyril |
| 18. | 7-[3-(1,2,4-Triazol-1-yl)propoxy]-3,4-dihydrocarbostyril |
| 19. | 5-[3-(1,2,4-Triazol-1-yl)propoxy-3,4-dihydrocarbostyril |
| 20. | 6-[3-(5-Methyl-2-imidazolyl)thiopropoxy]-3,4-dihydrocarbostyril |
| 21. | 6-[3-(5-Methoxybenzimidaol-2-yl)thiopropoxy]-3,4-dihydrocarbostyril monohydrate |
| 22. | 6-[3-(5-Phenyl-2-imidazolyl)thiopropoxy]-3,4-dihydrocarbostyril.½-oxalate |
| 23. | 7-[3-(1,3,4-Triazol-2-yl)thiopropoxy]-3,4-dihydrocarbostyril |
| 24. | 6-[3-(1-Ethyl-benzimidazol-2-yl)thiopropoxy]-3,4-dihydrocarbostyril.½-hydrate |
| 25. | 7-[2-(1,2,4-Triazol-1-yl)ethoxy]-3,4-dihydrocarbostyril |
| 26. | 7-[3-(2-Thiazolinyl)thiopropoxy]-3,4- |

-continued

| Test compound No. | |
|---|---|
| | dihydrocarbostyril |
| 27. | 7-[4-(1,2,4-Triazol-1-yl)butoxy]-3,4-dihydrocarbostyril |
| 28. | 7-[3-(1-Benzyl-2-imidazolyl)thiopropoxy]-3,4-dihydrocarbostyril |
| 29. | 7-[3-(1-Allyl-2-imidazolyl)thiopropoxy]-3,4-dihydrocarbostyril |
| 30. | 7-[3-(1-Ethyl-1,3,4-triazol-2-yl)thiopropoxy]-3,4-dihydrocarbostyril |
| 31. | 7-[3-(1-Ethyl-1,2,4-triazol-3-yl)thiopropoxy]-3,4-dihydrocarbostyril |
| 32. | 7-[3-(2-Pyridyl)thiopropoxy]-3,4-dihydrocarbostyril |
| 33. | 7-[5-(1,2,4-Triazol-1-yl)pentyloxy]-3,4-dihydrocarbostyril |
| 34. | 6-[4-(1,2,4-Triazol-1-yl)butyryl]-3,4-dihydrocarbostyril |
| 35. | 6-{3-[1-(2-Methylphenyl)-2-imidazolyl]-thiopropoxy}-3,4-dihydrocarbostyril |
| 36. | 6-[2-(1,2,4-Triazol-1-yl)ethoxy]-3,4-dihydrocarbostyril |
| 37. | 6-[4-(1,2,4-Triazol-1-yl)butoxy]-3,4-dihydrocarbostyril |
| 38. | 6-{3-[1-(3-Pyridyl)-2-imidazolyl]thiopropoxy}-3,4-dihydrocarbostyril |
| 39. | 6-{3-[1-(2-Methoxyphenyl)-2-imidazolyl]-thiopropoxy}-3,4-dihydrocarbostyril |
| 40. | 6-{3-[1-(4-Methylphenyl)-2-imidazolyl]-thiopropoxy}-3,4-dihydrocarbostyril |
| 41. | 6-{[3-(1,2,4-Triazolol-1-yl)propyl]amino}-3,4-dihydrocarbostyril |
| 42. | 6-{[3-(1,2,4-Triazol-1-yl)propyl]thio}-3,4-dihydrocarbostyril |
| 43. | 6-[2-(1,2,4-Triazol-1-yl)acetyl]-3,4-dihydrocarbostyril |
| 44. | 6-[2-(1-Phenyl-2-imidazol)thioacetyl]-3,4-dihydrocarbostyril |
| 45. | 6-[2-(1-Phenyl-2-imidazolyl)thioacetyl]-carbostyril |
| 46. | 6-[2-(1-Imidazolyl)acetyl]-3,4-dihydrocarbostyril hydrobromide |
| 47. | 6-[2-(3-Methyl-1-pyrrazolyl)acetyl]-3,4-dihydrocarbostyril |
| 48. | 6-[2-(2-Methylthio-4-methyl-1-imidazolyl)-acetyl]-3,4-dihydrocarbostyril |
| 49. | 6-[1-Hydroxy-2-(1-phenyl-2-imidazolyl)-thioethyl]-3,4-dihydrocarbostyril |
| 50. | 6-[2-(1-Ethyl-2-imidazolyl)thioacetyl]-3,4-dihydrocarbostyril |
| 51. | 6-[2-(1-Allyl-2-imidazolyl)thioacetyl]-3,4-dihydrocarbostyril |
| 52. | 6-[1-Hydroxy-4-(1-phenyl-2-imidazolyl)-thiobutyl]-3,4-dihydrocarbostyril |
| 53. | 6-[1-Hydroxy-3-(1-phenyl-2-imidazolyl)-thiopropyl]-3,4-dihydrocarbostyril |
| 54. | 6-{2-[1-(3-Trifluoromethylphenyl)-2-imidazolyl]thioacetyl}-3,4-dihydrocarbostyril |
| 55. | 6-{2-[1-(2-Methylphenyl)-2-imidazolyl]-thioacetyl}-3,4-dihydrocarbostyril |
| 56. | 6-[2-(1-Phenyl-2-imidazolyl)thiobutyryl]-3,4-dihydrocarbostyril |
| 57. | 7-[3-(1,2,4-Triazol-1-yl)propox-]carbostyril |

TABLE 1

| Test compound No. | Inhibition rate (%) |
|---|---|
| 1 | 14 |
| 2 | 62 |
| 3 | 100 |
| 4 | 40 |
| 5 | 60 |
| 6 | 67 |
| 7 | 41 |
| 8 | 66 |
| 9 | 40 |

TABLE 1-continued

| Test compound No. | Inhibition rate (%) |
|---|---|
| 10 | 95 |
| 11 | 41 |
| 12 | 61 |
| 13 | 65 |
| 14 | 50 |
| 15 | 68 |
| 16 | 71 |
| 17 | 28 |
| 18 | 83 |
| 19 | 23 |
| 20 | 47 |
| 21 | 26 |
| 22 | 41 |
| 23 | 50 |
| 24 | 27 |
| 25 | 85 |
| 26 | 21 |
| 27 | 89 |
| 28 | 31 |
| 29 | 48 |
| 30 | 52 |
| 31 | 52 |
| 32 | 53 |
| 33 | 84 |
| 34 | 44 |
| 35 | 62 |
| 36 | 69 |
| 37 | 56 |
| 38 | 86 |
| 39 | 42 |
| 40 | 15 |
| 41 | 34 |
| 42 | 57 |
| 43 | 33 |
| 44 | 65 |
| 45 | 35 |
| 46 | 30 |
| 47 | 25 |
| 48 | 45 |
| 49 | 66 |
| 50 | 34 |
| 51 | 40 |
| 52 | 22 |
| 53 | 35 |
| 54 | 35 |
| 55 | 75 |
| 56 | 40 |
| 57 | 70 |

REFERENCE EXAMPLE 1

10 Grams (39.7 mM) of 6-(4-chlorobutyryl)-3,4-dihydrocarbostyril was dissolved in 300 ml of benzene, then to this solution was added 7.4 g (120 mM) of ethylene glycol and 300 mg of p-toluenesulfonic acid, and the whole mixture was refluxed by heating under dehydrating in Dean-Stark extractor for 6 hours. The reaction mixture was cooled and neutralized with an aqueous solution saturated with sodium hyfrogen carbonate, then extracted with chloroform. The chloroform extract was washed with water then dried with anhydrous magnesium sulfate, then concentrated by removing the solvent by evaporation. The residue thus obtained was purified by means of a silicagel column chromatography (eluent: chloroform:methanol=40:1) to yield 10.5 g of 6-(1-ethylenedioxy-4-chlorobutyl)-3,4-dihydrocarbostyril.

REFERENCE EXAMPLE 2

28 Grams of methyl cyclohexylcarboxylate and 15 g of 85%-NH$_2$NH$_2$.H$_2$O were dissolved in 50 ml of isopropyl alcohol, and the solution was refluxed by heating for 10 hours. The reaction mixture was concentrated, and the crystals precipitated by adding water were collected by filtration, then the crystals were washed with water, then recrystallized from water to yield 20 g of cyclohexanecarbohydrazide in the form of colorless needle-like crystals.

Melting point: 155.5°–156.5° C.

EXAMPLE 1

2.0 Grams (7.0 mM) of 6-(3-bromopropoxy)-3,4-dihydrocarbostyril, 2.2 g (7.7 mM) of 2-methylimidazol and 1.3 ml (8.4 mM) of DBU were dissolved in 80 ml of isopropanol, and the resulting solution was refluxed by heating for 20 hours. The reaction mixture was concentrated, and to the resulting residue was added water, then extracted with chloroform. The chloroform extract was washed with water, dried with anhydrous sodium sulfate, then concentrated. The resulting residue was purified by means of a silica gel column chromatography (eluent: dichloromethane:methanol=20:1), and recrystallized from ethanol-n-hexane to yield 1.0 g of 6-[3-(2-methyl-1-imidazolyl)propoxy]-3,4-dihydrocarbostyril. White powdery substance.

Melting point: 141.5°–142.5° C.

EXAMPLE 2

2.4 Grams (13.4 mM) of 6-mercapto-3,4-dihydrocarbostyril, 3.3 g (17.4 mM) of 1-(3-bromopropyl)-1,2,4-triazol, and 2.6 ml (17.4 mM) of DBU were added to 60 ml of isopropanol, and the whole mixture was refluxed by heating for 2 hours. After the reaction was completed, the reaction mixture was concentrated, the resulting residue was extracted with chloroform. The chloroform extract was washed with water, an aqueous solution saturated with sodium hydrogen carbonate, and water in this order, then dried with anhydrous sodium sulfate. The dried extract was concentrated by removing the solvent by evaporation, the residue was purified by means of a silica gel column chromatography (eluent: dichloromethane: methanol=20:1), and recrystallized from ethanol-n-hexane to yield 2.5 g of 6-[3-(1H-1,2,4-triazol-1-yl)propylthio]-3,4-dihydrocarbostyril. Colorless needle-like crystals.

Melting point: 114.5°–115.5° C.

EXAMPLES 3–68

By using suitable starting materials, and by procedures similar to those of described in Examples 1 and 2, there were prepared compounds shown in the following Table 2.

TABLE 2

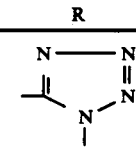

| Example No. | $R^1$ | —Z—A— | $(X)_n$ | R | Position of the side-chain* | 3,4-carbon-carbon bond |
|---|---|---|---|---|---|---|
| 3 | H | —O(CH$_2$)$_3$— | S | 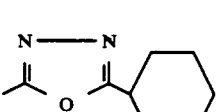 | 6 | Single bond |
| 4 | H | —O(CH$_2$)$_3$— | — | 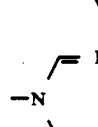 | 6 | Single bond |
| 5 | H | —O(CH$_2$)$_3$— | — | 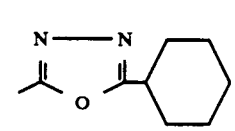 | 6 | Double bond |
| 6 | H | —O(CH$_2$)$_3$— | — | 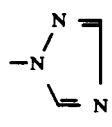 | 6 | Double bond |
| 7 | H | —O(CH$_2$)$_3$— | — | 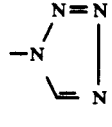 | 6 | Single bond |
| 8 | H | —O(CH$_2$)$_3$— | — | N=N / —N \ N | 6 | Single bond |

TABLE 2-continued

Z—A—(X)$_n$—R on quinolin-2(1H)-one core with NR$^1$

| | | | | R | | |
|---|---|---|---|---|---|---|
| 9 | H | —O(CH$_2$)$_3$— | — | 1,2,4-triazol-1-yl (N—N=CH—N=CH) | 6 | Double bond |
| 10 | H | —O(CH$_2$)$_3$— | — | 2-methylimidazol-1-yl | 6 | Double bond |
| 11 | H | —O(CH$_2$)$_3$— | — | 1,2,3-triazol-1-yl | 6 | Double bond |
| 12 | H | —O(CH$_2$)$_3$— | — | tetrazol-2-yl | 6 | Double bond |
| 13 | H | —O(CH$_2$)$_3$— | S | 2-methyl-1-phenylimidazol-1-yl | 6 | Single bond |
| 14 | H | —O(CH$_2$)$_3$— | — | imidazol-1-yl | 6 | Single bond |
| 15 | H | —O(CH$_2$)$_3$— | S | 5-methyl-1-phenyl-1,2,4-triazol-1-yl | 6 | Single bond |
| 16 | H | —O(CH$_2$)$_3$— | S | 2-methylimidazol (NH) | 6 | Single bond |
| 17 | H | —O(CH$_2$)$_3$— | S | 2-methyl-1-ethylimidazole | 6 | Single bond |
| 18 | H | —O(CH$_2$)$_3$— | — | 1,2,4-triazol-1-yl | 6 | Single bond |

TABLE 2-continued

Z—A—(X)$_n$—R on quinolinone scaffold with NR$^1$, =O

| No. | R$^1$ | A | X | R | n | Z |
|---|---|---|---|---|---|---|
| 19 | H | —O(CH$_2$)$_3$— | — | 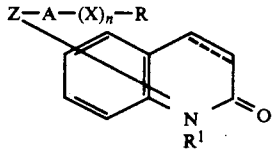 1,2,4-triazolyl (N-linked) | 7 | Single bond |
| 20 | H | —O(CH$_2$)$_3$— | — | 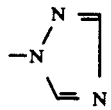 1,2,4-triazolyl (N-linked) | 5 | Single bond |
| 21 | H | —O(CH$_2$)$_3$— | S | 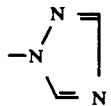 2-methyl-5-methyl-imidazolyl | 6 | Single bond |
| 22 | H | —O(CH$_2$)$_3$— | S | 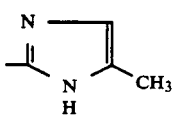 2-methyl-5-methoxy-benzimidazolyl | 6 | Single bond |
| 23 | H | —O(CH$_2$)$_3$— | S | 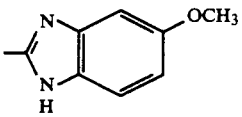 2-methyl-5-phenyl-imidazolyl | 6 | Single bond |
| 24 | H | —O(CH$_2$)$_3$— | S | 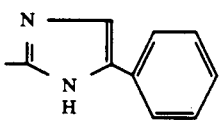 3-methyl-1,2,4-triazolyl | 7 | Single bond |
| 25 | H | —O(CH$_2$)$_3$— | S | 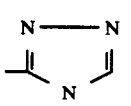 1-ethyl-2-methyl-benzimidazolyl | 6 | Single bond |
| 26 | H | —O(CH$_2$)$_2$— | — | 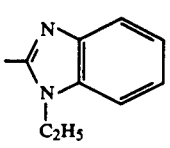 1,2,4-triazolyl (N-linked) | 7 | Single bond |
| 27 | H | —O(CH$_2$)$_3$— | S | 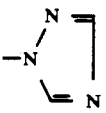 2-methyl-4,5-dihydrothiazolyl | 7 | Single bond |
| 28 | H | —O(CH$_2$)$_4$— | — | 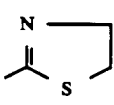 1,2,4-triazolyl (N-linked) | 7 | Single bond |
| 29 | H | —O(CH$_2$)$_3$— | S | 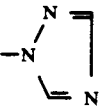 1-benzyl-2-methyl-imidazolyl | 7 | Single bond |

TABLE 2-continued

Z—A—(X)$_n$—R on quinolin-2(1H)-one core with N—R$^1$

| No. | Z | A—(X)$_n$— | X | R | Position | Bond |
|---|---|---|---|---|---|---|
| 30 | H | —O(CH$_2$)$_3$— | S | imidazole with CH$_2$CH=CH$_2$ on N | 7 | Single bond |
| 31 | H | —O(CH$_2$)$_3$— | S | 1,2,4-triazole with C$_2$H$_5$ on N | 7 | Single bond |
| 32 | H | —O(CH$_2$)$_3$— | S | 1,2,4-triazole with N—C$_2$H$_5$ | 7 | Single bond |
| 33 | H | —O(CH$_2$)$_3$— | S | pyridin-2-yl | 7 | Single bond |
| 34 | H | —O(CH$_2$)$_5$— | — | 1,2,4-triazol-1-yl | 7 | Single bond |
| 35 | H | —O(CH$_2$)$_3$— | S | imidazole with 2-methylphenyl on N | 6 | Single bond |
| 36 | H | —O(CH$_2$)$_2$— | — | 1,2,4-triazol-1-yl | 6 | Single bond |
| 37 | H | —O(CH$_2$)$_4$— | — | 1,2,4-triazol-1-yl | 6 | Single bond |
| 38 | H | —O(CH$_2$)$_3$— | S | imidazole with pyridin-3-yl on N | 6 | Single bond |

TABLE 2-continued

Z—A—(X)ₙ—R on quinolin-2(1H)-one core with N—R¹

| | R¹ | A | X | R | position | bond |
|---|---|---|---|---|---|---|
| 39 | H | —O(CH₂)₃— | S | 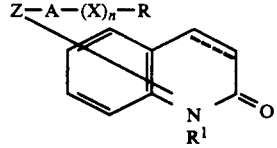 (1-(2-methoxyphenyl)imidazol-2-yl) | 6 | Single bond |
| 40 | H | —O(CH₂)₃— | S | 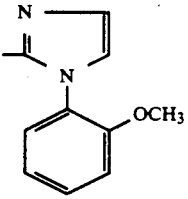 (1-(4-methylphenyl)imidazol-2-yl) | 6 | Single bond |
| 41 | H | —NH(CH₂)₃— | — | 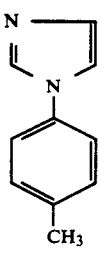 (1,2,4-triazol-1-yl) | 6 | Single bond |
| 42 | H | —O(CH₂)₃— | O | 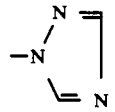 (1-phenylimidazol-2-yl) | 6 | Single bond |
| 43 | C₂H₅ | —O(CH₂)₃— | — | 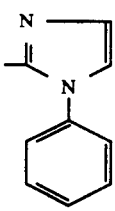 (1,2,4-triazol-1-yl) | 6 | Single bond |
| 44 | —CH₂—C₆H₅ | —O(CH₂)₃— | — | 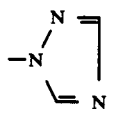 (1,2,4-triazol-1-yl) | 6 | Single bond |
| 45 | H | —O(CH₂)₃— | — | 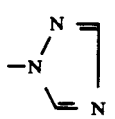 (tetrazol-1-yl) | 6 | Single bond |
| 46 | H | —O(CH₂)₃— | — | 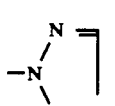 (pyrrol-1-yl) | 6 | Single bond |
| 47 | H | —O(CH₂)₃— | — | 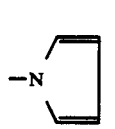 (2-(phenylthio)pyrrol-1-yl) | 6 | Single bond |

TABLE 2-continued
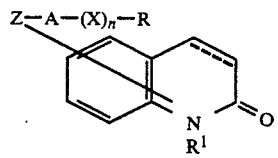
| | $R^1$ | A | X | R | (position) | Z |
|---|---|---|---|---|---|---|
| 48 | H | —O(CH₂)₃— | — | ![phenyl-imidazole] | 6 | Single bond |
| 49 | H | —O(CH₂)₃— | — | ![S,N-phenyl triazole] | 6 | Single bond |
| 50 | H | —O(CH₂)₃— | — | ![S,phenyl triazole] | 6 | Single bond |
| 51 | H | —O(CH₂)₃— | — | ![S-phenyl triazole] | 6 | Single bond |
| 52 | H | —O(CH₂)₃— | S | ![benzimidazole] | 6 | Single bond |
| 53 | H | —O(CH₂)₃— | S | ![pyrimidine] | 7 | Single bond |
| 54 | H | —O(CH₂)₃— | S | ![imidazole-NH] | 7 | Single bond |
| 55 | H | —O(CH₂)₃— | S | ![imidazole-N-C₂H₅] | 7 | Single bond |

TABLE 2-continued

Z—A—(X)ₙ—R on quinolin-2(1H)-one core with R¹ on N

| No. | R¹ | A | X | R | position | bond |
|---|---|---|---|---|---|---|
| 56 | H | —O(CH₂)₃— | S | 2-methyl-1-phenyl-imidazol-yl | 7 | Single bond |
| 57 | H | —O(CH₂)₃— | S | 2-methyl-1-(3-trifluoromethylphenyl)imidazol-yl | 7 | Single bond |
| 58 | H | —O(CH₂)₃— | S | 2-methyl-1-(4-methoxyphenyl)imidazol-yl | 7 | Single bond |
| 59 | H | —O(CH₂)₃— | S | 2-methyl-1-(4-dimethylaminophenyl)imidazol-yl | 7 | Single bond |
| 60 | H | —O(CH₂)₃— | S | 1-(4-chlorophenyl)imidazol-yl | 7 | Single bond |
| 61 | H | —O(CH₂)₃— | S | 3-methyl-1-benzyl-1,2,4-triazol-yl | 7 | Single bond |
| 62 | H | —O(CH₂)₃— | S | 5-methyl-2-benzyl-1,2,4-triazol-yl | 7 | Single bond |

TABLE 2-continued

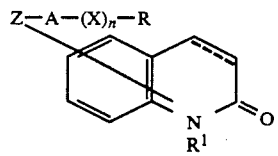

| | | | | | | |
|---|---|---|---|---|---|---|
| 63 | H | —O(CH$_2$)$_3$— | S | N=N, N=N, N-phenyl (1-phenyltetrazol-5-yl) | 6 | Single bond |
| 64 | H | —O(CH$_2$)$_3$— | S | N=N, N=N, N-CH$_3$ (1-methyltetrazol-5-yl) | 6 | Double bond |
| 65 | H | —O(CH$_2$)$_2$— | S | N=N, N=N, N-phenyl (1-phenyltetrazol-5-yl) | 6 | Single bond |
| 66 | H | —O(CH$_2$)$_3$— | — | —N(triazolyl) | 3 | Double bond |
| 67 | H | —O(CH$_2$)$_2$— | — | pyrazolinone with CH$_3$ | 6 | Single bond |
| 68 | H | —O(CH$_2$)$_3$— | — | —N(triazolyl) | 4 | Double bond |

*Side-chain: —Z—A—(X)$_n$—R

| Example No. | Crystal form (Recrystallization solvent) | Melting point (°C.) | Salt |
|---|---|---|---|
| 3 | Colorless needles (Chloroform) | 166.0–168.0 | — |
| 4 | White powder (Chloroform-diethyl ether) | 111.5–112.5 | — |
| 5 | White powder (Methanol-diethyl ether) | 281.0–282.0 | HCl |
| 6 | Yellow needles (Chloroform-petroleum ether) | 160.0–161.5 | — |
| 7 | Colorless needles (Chloroform-petroleum ether) | 120.5–122.0 | — |
| 8 | Colorless needles (Ethanol-diethyl ether) | 151.0–152.0 | — |
| 9 | Colorless needles (Ethanol) | 179.5–181.0 | — |
| 10 | Colorless needles (Chloroform-diethyl ether) | 235.0–237.0 (decomp.) | — |
| 11 | Colorless needles (Ethanol-diethyl ether) | 179.5–181.5 | — |
| 12 | Colorless needles (Chloroform-methanol-diethyl ether) | 213.0–214.0 (decomp.) | — |
| 13 | Colorless needles | 165.0–166.0 | — |

TABLE 2-continued

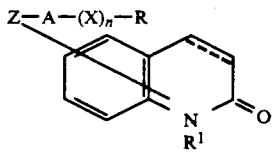

| | | | |
|---|---|---|---|
| | (Ethanol-diethyl ether-n-hexane) | | |
| 14 | Colorless prisms | 102.0–10.35 | — |
| | (Dichloromethane-n-hexane) | | |
| 15 | Colorless needles | 189.0–190.0 | — |
| | (Chloroform-methanol-n-hexane) | | |
| 16 | Colorless needles | 183.0–184.0 | — |
| | (Chloroform-methanol-n-hexane) | | |
| 17 | Colorless needles | 120.5–121.0 | — |
| | (Ethanol-n-hexane) | | |
| 18 | Colorless needles | 136.0–137.0 | — |
| | (Ethanol-n-hexane) | | |
| 19 | Colorless needles | 132.0–133.5 | — |
| | (Ethanol-n-hexane) | | |
| 20 | Colorless prisms | 211.0–222.0 | — |
| | (Chloroform-methanol-n-hexane) | | |
| 21 | Colorless prisms | 221.0–222.0 | — |
| | (Chloroform-methanol-n-hexane) | | |
| 22 | White powder | 154.5–156.0 | $H_2O$ |
| | (Ethanol-n-hexane) | | |
| 23 | White powder | 74.0–80.0[1] | ½(COOH)$_2$ |
| | (Acetone-water) | | |
| 24 | Colorless needles | 143.0–144.5 | — |
| | (Ethanoyl-n-hexane) | | |
| 25 | Colorless needles | 131.5–132.5 | ½$H_2O$ |
| | (Ethanol-n-hexane) | | |
| 26 | Colorless needles | 187.5–189.5 | — |
| | (Ethanol-n-hexane) | | |
| 27 | White powder | 114.5–115.0 | — |
| | (Chloroform-n-hexane) | | |
| 28 | Colorless needles | 109.0–110.0 | — |
| | (Ethanol-n-hexane) | | |
| 29 | Colorless needles | 114.5–115.5 | — |
| | (Ethanol-n-hexane) | | |
| 30 | Colorless needles | 75.5–76.5 | — |
| | (Ethanol-n-hexane) | | |
| 31 | Colorless needles | 119.0–120.0 | — |
| | (Ethanol-n-hexane) | | |
| 32 | Colorless needles | 93.0–94.0 | — |
| | (Ethanol-n-hexane) | | |
| 33 | Light yellow prisms | 121.5–122.5 | — |
| | (Ethanol-n-hexane) | | |
| 34 | Colorless granules | 121.0–122.0 | — |
| | (Ethanol-n-hexane) | | |
| 35 | Colorless prisms | 136.5–137.0 | — |
| | (Ethanol-n-hexane) | | |
| 36 | Colorless needles | 164.0–165.0 | — |
| | (Ethanol-n-hexane) | | |
| 37 | Colorless needles | 131.0–132.0 | — |
| | (Ethanol-n-hexane) | | |
| 38 | Colorless needles | 164.5–166.0 | — |
| | (Ethanol-n-hexane) | | |
| 39 | Colorless needles | 128.0–129.0 | — |
| | (Ethanol-n-hexane) | | |
| 40 | Colorless needles | 143.5–144.0 | — |
| | (Ethanol-n-hexane) | | |
| 41 | Light yellow needles | 118.5–119.5 | — |
| | (Ethyl acetate-n-hexane) | | |
| 42 | Light yellow powder | 187.0–189.0 | — |
| | (Ethanol-n-hexane) | | |
| 43 | Colorless needles | 97.0–98.0 | — |
| | (Ethyl acetate-n-hexane) | | |
| 44 | Colorless needles | 98.0–99.0 | — |
| | (Ethyl acetate-n-hexane) | | |
| 45 | Colorless needles | 129.5–130.0 | — |
| | (Ethanol-diethyl ether) | | |
| 46 | Light yellow needles | 127.5–130.0 | — |
| | (Chloroform-diethyl ether) | | |
| 47 | Light brown prisms | 123.5–124.5 | — |
| | (Ethanol-n-hexane) | | |
| 48 | Light yellow needles | 161.0–162.0 | — |
| | (Ethyl acetate) | | |
| 49 | Colorless needles | 150.5–151.5 | — |
| | (Ethanol-n-hexane) | | |
| 50 | Colorless needles | 105.0–106.5 | — |

TABLE 2-continued

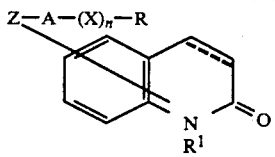

| | | | |
|---|---|---|---|
| | (Ethanol-n-hexane) | | |
| 51 | Colorless flakes | 119.5–200.5 | — |
| | (Ethanol-n-hexane) | | |
| 52 | Colorless needles | 217.0–218.0 | — |
| | (Chloroform-methanol-n-hexane) | | |
| 53 | Colorless flakes | 122.0–123.5 | — |
| | (Ethanol-n-hexane) | | |
| 54 | Colorless needles | 165.5–167.0 | — |
| | (Ethanol-n-hexane) | | |
| 55 | Colorless needles | 112.5–113.0 | — |
| | (Ethanol-n-hexane) | | |
| 56 | Colorless needles | 101.5–102.0 | — |
| | (Ethanol-n-hexane) | | |
| 57 | Colorless needles | 85.5–86.0 | — |
| | (Ethanol-n-hexane) | | |
| 58 | Colorless needles | 127.0–128.0 | — |
| | (Ethanol-n-hexane) | | |
| 59 | Colorless needles | 113.5–115.0 | — |
| | (Ethanol-n-hexane) | | |
| 60 | Colorless needles | 102.0–103.0 | — |
| | (Ethanol-n-hexane) | | |
| 61 | Colorless needles | 121.0–122.0 | — |
| | (Ethanol-n-hexane) | | |
| 62 | Colorless needles | 118.0–119.0 | — |
| | (Ethanol-n-hexane) | | |
| 63 | Colorless needles | 148.5–149.5 | — |
| | (Chloroform-methanol) | | |
| 64 | Colorless needles | 204–206.5 | — |
| | (Methanol) | | |
| 65 | Colorless needles | 163–164 | — |
| | (Ethanol) | | |
| 66 | Colorless needles | 157–158 | — |
| | (Ethanol-diethyl ether) | | |
| 67 | Light yellow granules | 175–176 | — |
| | (Ethanol) | | |
| 68 | Colorless prisms | 210–211 | — |
| | (Ethanol) | | |

[1]NMR (DMSO-$d_6$) δ: 1.82–2.24 (2H, m), 2.25–2.60 (2H, m), 2.65–3.00 (2H, m), 3.20 (1H, t, J=7Hz), 4.02 (2H, t, J=6Hz), 6.56–6.97 (3H, m), 6.56–6.97 (3H, m), 7.07–7.88 (6H, m), 9.88 (1H, brs).

EXAMPLE 69

10.5 Grams (35.5 mM) of 6-(1-ethylenedioxy-4-chlorobutyl)-3,4-dihydrocarbostyril was dissolved in 10.6 g (71 mM) of dimethylformamide, to this solution was added 10.6 g (71 mM) of sodium iodide, 5.4 g (78.1 mM) of 1H-1,2,4-triazol and 6.5 ml (46.2 mM) of DBU, and the whole mixture was heated at 80° C. for 7 hours with stirring. The reaction mixture was concentrated by removing the solvent by evaporation under reduced pressure, the residue was extracted with chloroform. The chloroform extract was washed with water, dried with anhydrous magnesium sulfate, then concentrated. The resulting residue was purified by means of a silica gel column chromatography (eluent: chloroform:methanol=40:1), and recrystallized from ethanol-n-hexane to yield 8.0 g of 6-[1-ethylenedioxy-4-(1H-1,2,4-triazol-1-yl)butyl]-3,4-dihydrocarbostyril. Next, to a solution of 1 g (3.0 mM) of 6-[1-ethylenedioxy-4-(1H-1,2,4-triazol-1-yl)butyl]-3,4-dihydrocarbostyril with 10 ml of DMF was added 3 ml of 5%-hydrochloric acid and stirred for 2 hours at room temperature. After concentration by removal of the solvent, the residue was extracted with chloroform: methanol=3:1. The extract was washed with water, dried with an anhydrous magnesium sulfate, then concentrated by removal of the solvent. The resulting residue was recrystallized from chloroform-ethanol to yield 6-[4-(1H-1,2,4-triazol-1-yl)butyryl]-3,4-dihydrocarbostyril.

Colorless needle-like crystals.

Melting point: 194.0°–195.0° C.

By using suitable starting materials, and by using procedures similar to those described in Example 69, there were prepared compounds of the above-mentioned Examples 5, 7–12, 14, 18–20, 26, 28, 34, 36, 37, 41, 43–51 and compounds of Examples 169–170, as well as prepared compounds of Examples 70–84 shown in the Tables 3 as follows.

EXAMPLES 70–84

TABLE 3

Z—A—(X)ₙ—R structure with N-R¹ and =O

| Example No. | R¹ | —Z—A— | (X)ₙ | R | Position of the side-chain* | 3,4-carbon bond | Crystal form (Recrystallization solvent) | Melting point (°C.) | Salt |
|---|---|---|---|---|---|---|---|---|---|
| 70 | H | —COCH₂— | — |  | 6 | Single bond | Light yellow needles (methanol-water) | 244.0–248.0 | — |
| 71 | H | —COCH₂— | — |  | 6 | Single bond | Light yellow powder (Dimethylformamide) | 302.0–303.0 | HBr |
| 72 | H | —COCH₂— | — |  | 6 | Single bond | Light brown plates (Ethanol) | 207.0–208.0 | — |
| 73 | H | —COCH₂— | — |  | 6 | Single bond | White powder (Ethanol-water) | 206.0–207.0 | — |
| 74 | H | —COCH₂— | — | 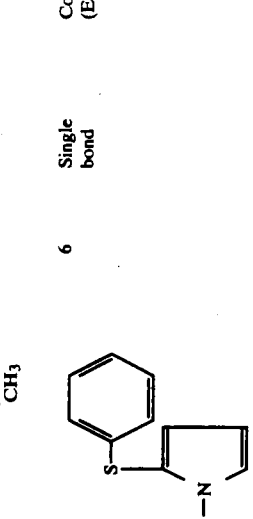 | 6 | Single bond | Colorless needles (Ethanol-water) | 158.0–159.0 | — |

TABLE 3-continued

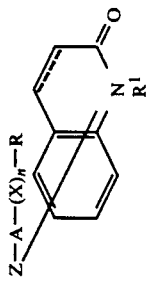

| Example No. | R¹ | —Z—A— | (X)ₙ | R | Position of the side-chain* | 3,4-carbon-carbon bond | Crystal form (Recrystallization solvent) | Melting point (°C.) | Salt |
|---|---|---|---|---|---|---|---|---|---|
| 75 | H | —COCH₂— | — | (phenylthio-imidazole) | 6 | Single bond | Colorless prisms (Methanol-water) | 259.5–262.5 (decomp.) | HCl |
| 76 | H | —COCH₂— | — | (phenyl-imidazole) | 6 | Single bond | Colorless powder (Chloroform-methanol-ethyl acetate) | 234.0–235.0 | H₂O |
| 77 | H | —COCH₂— | — | (triazole) | 6 | Single bond | Light yellow granules (Dimethylformamide) | 296 (decomp.) | — |
| 78 | H | —COCH₂— | — | (CO₂H, CH₃ imidazole) | 6 | Single bond | Yellow needles (Ethanol) | 224 (decomp.) | HCl·H₂O |

TABLE 3-continued

| Example No. | $R^1$ | –Z–A– | $(X)_n$ | R | Position of the side-chain* | 3,4-carbon- carbon bond | Crystal form (Recrystallization solvent) | Melting point (°C.) | Salt |
|---|---|---|---|---|---|---|---|---|---|
| 79 | H | –COCH$_2$– | — | (imidazole with CH$_3$, C$_2$H$_5$) | 6 | Single bond | Colorless needles (Ethanol) | 233–234 | — |
| 80 | H | –COCH$_2$– | — | (imidazole with CN, NH$_2$) | 6 | Single bond | White powder (Chloroform-ethanol) | 265–266 | — |
| 81 | H | –COCH$_2$– | — | (imidazole with CO$_2$C$_2$H$_5$, CH$_3$) | 6 | Single bond | Light yellow needles (Ethanol) | 234–235 | — |
| 82 | H | –COCH$_2$– | — | (thiazole with phenyl) | 5 | Single bond | Colorless granules (Methanol) | 264–266 | $R^2$ = OH (8-position) |

TABLE 3-continued

Side-chain: —Z—A—(X)ₙ—R (attached to bicyclic ring with N—R¹ and C=O)

| Example No. | R¹ | —Z—A— | (X)ₙ | R | Position of the side-chain* | 3,4-carbon- carbon bond | Crystal form (Recrystallization solvent) | Melting point (°C.) | Salt |
|---|---|---|---|---|---|---|---|---|---|
| 83 | H | —COCH₂— | — | (thiazole with phenylthio substituent) | 5 | Single bond | Colorless needles (Ethanol) | 212 | R² = OCH₃ (8-position) |
| 84 | H | —COCH₂— | — | (5-hydroxy-3-methylpyrazole) | 6 | Single bond | White powder (Chloroform-methanol) | 234–235 | — |

*Side-chain: —Z—A—(X)ₙ—R

EXAMPLE 85

2.24 Grams (10 mM) of 6- -chloroacetyl-3,4-dihydrocarbostyril, 1.94 g (11 mM) of 1-phenyl-2-mercaptoimidazol and 1.75 ml (12 mM) of DBU were added to 80 ml of isopropanol, then the mixture was refluxed by heating for 10 minutes. After cooling the reaction mixture, the crystals formed in the reaction mixture were collected by filtration, and washed with isopropanol. Recrystallized from ethanol to yield 6-[2-(1-phenyl-2-imidazolyl)thioacetyl]-3,4-dihydrocarbostyril. Light yellow needle-like crystals.

Melting point: 209.0°–210.0° C.

EXAMPLE 86

2.0 Grams (6.8 mM) of 6-(2-bromobutyryl)-3,4-dihydrocarbostyril, 1.4 g (8.1 mM) of 1-phenyl-2-mercaptoimidazol and 1.1 ml (8.1 mM) of DBU were added to 60 ml of isopropanol and the mixture was refluxed by heating for 3 hours. After the reaction was completed, the reaction mixture was concentrated by removal of the solvent, the residue thus obtained was extracted with chloroform. The chloroform extract was washed with water, then dried with anhydrous sodium sulfate and concentrated by removing of the solvent. The residue thus obtained was purified by means of a silica gel column chromatography (eluent: dichloromethane:methanol=20:1), recrystallized from chloroform-n hexane to yield 2 g of 6-[2-(1-phenyl-2-imidazolul)thiobutyryl]-3,4-dihydrocarbostyril. Colorless needle-like crystals. 1 Melting point: 82.0°–84.5° C.

By using suitable starting materials and by procedures similar to those described in Examples 85 and 86, there were prepared compounds of Examples 3, 13, 15–17, 21–25, 27, 29–33, 38–40, 42, 52–65, and compound of Examples 175–178, 179–184, 185 186, 187–191-202. Furthermore, there were prepared compound of Examples 87–140 as shown in the following Table 4.

EXAMPLES 87–140

TABLE 4

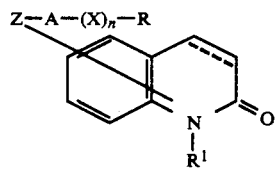

| Example No. | $R^1$ | —Z—A— | $(X)_n$ | R | Position of the side-chain* | 3,4-carbon-carbon bond |
|---|---|---|---|---|---|---|
| 87 | H | —COCH$_2$— | S | N-phenyl imidazolyl | 6 | Double bond |
| 88 | H | —CH(OH)CH$_2$— | S | N-phenyl imidazolyl | 6 | Single bond |
| 89 | H | —COCH$_2$— | S | N-ethyl imidazolyl | 6 | Single bond |
| 90 | H | —COCH$_2$— | S | N-allyl imidazolyl | 6 | Single bond |
| 91 | H | —CH(OH)(CH$_2$)$_3$— | S | N-phenyl imidazolyl | 6 | Single bond |

TABLE 4-continued

| 92 | H | OH<br>—CH(CH₂)₂— | S | [2-phenyl-imidazol-1-yl] | 6 | Single bond |
| 93 | H | —COCH₂— | | [2-(3-trifluoromethylphenyl)-imidazol-1-yl] | 6 | Single bond |
| 94 | H | —COCH₂— | S | [2-(2-methylphenyl)-imidazol-1-yl] | 6 | Single bond |
| 95 | H | OCH₃<br>—CHCH₂— | S | [2-phenyl-imidazol-1-yl] | 6 | Single bond |
| 96 | H | N—OH<br>—CCH₂— | S | [2-phenyl-imidazol-1-yl] | 6 | Single bond |
| 97 | H | —COCH₂— | O | [2-phenyl-imidazol-1-yl] | 6 | Single bond |
| 98 | H | —COCH₂— | SO | [2-phenyl-imidazol-1-yl] | 6 | Single bond |

TABLE 4-continued

| | | | | | | |
|---|---|---|---|---|---|---|
| 99 | H | —COCH$_2$— | SO$_2$ | 1-phenyl-2-imidazolyl | 6 | Single bond |
| 100 | C$_2$H$_5$ | —COCH$_2$— | S | 1-phenyl-2-imidazolyl | 6 | Single bond |
| 101 | H | —COCH$_2$— | S | 1-phenyl-2-imidazolyl | 7 | Single bond |
| 102 | H | —CO(CH$_2$)$_2$— | S | 1-phenyl-2-imidazolyl | 6 | Single bond |
| 103 | H | —CO(CH$_2$)$_3$— | S | 1-phenyl-2-imidazolyl | 6 | Single bond |
| 104 | H | —COCH$_2$— | S | 2-pyridyl | 6 | Single bond |
| 105 | H | —COCH$_2$— | S | 2-pyrimidinyl | 6 | Single bond |
| 106 | H | —COCH$_2$— | S | 1H-2-pyrrolyl | 6 | Single bond |
| 107 | H | —COCH$_2$— | S | 1-ethyl-2-pyrrolyl | 6 | Single bond |

TABLE 4-continued
| | | | | | | |
|---|---|---|---|---|---|---|
| 108 | H | —COCH₂— | S | 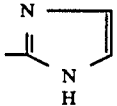 | 6 | Single bond |
| 109 | H | —COCH₂— | S | 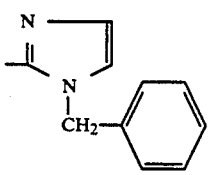 | 6 | Single bond |
| 110 | H | —COCH₂— | S | 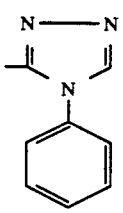 | 6 | Single bond |
| 111 | H | —COCH₂— | S | 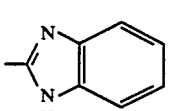 | 6 | Single bond |
| 112 | H | —COCH₂— | S | 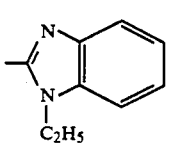 | 6 | Single bond |
| 113 | H | —COCH₂— | S |  | 6 | Single bond |
| 114 | H | —COCH₂— | S | 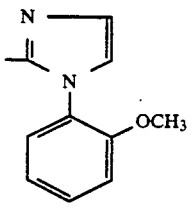 | 6 | Single bond |
| 115 | H | —COCH₂— | S | 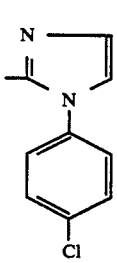 | 6 | Single bond |
| 116 | H | —COCH₂— | S | 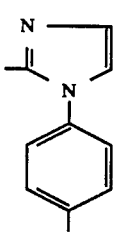 | 6 | Single bond |

TABLE 4-continued
| 117 | H | —COCH₂— | S | 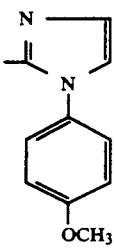 | 6 | Single bond |
| 118 | H | —COCH₂— | S | 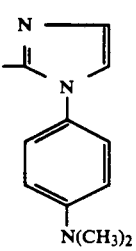 | 6 | Single bond |
| 119 | H | —COCH₂— | S | 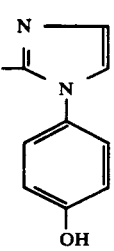 | 6 | Single bond |
| 120 | H | —COCH₂— | S | 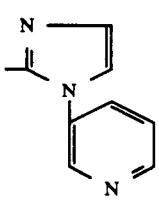 | 6 | Single bond |
| 121 | H | —COCH₂— | S | 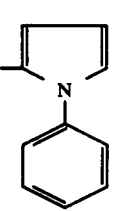 | 6 | Single bond |
| 122 | H | —COCH₂— | S | 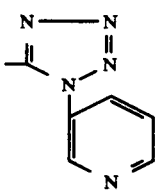 | 6 | Single bond |
| 123 | H | —COCH₂— | S | 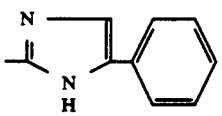 | 6 | Single bond |

TABLE 4-continued
| 124 | H | —CO(CH$_2$)$_2$— | S | 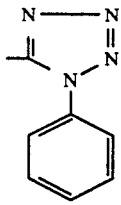 | 6 | Single bond |
| 125 | H | —CO(CH$_2$)$_3$— | S | 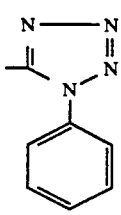 | 6 | Single bond |
| 126 | H | —COCH$_2$— | S | 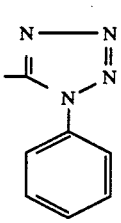 | 6 | Single bond |
| 127 | H | —COCH$_2$— | S | 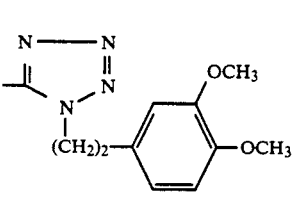 | 6 | Single bond |
| 128 | H | —COCH$_2$— | S | 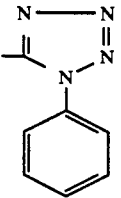 | 6 | Single bond |
| 129 | H | —COCH$_2$— | S | 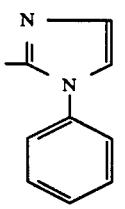 | 3 | Single bond |
| 130 | H | —COCH$_2$— | S | 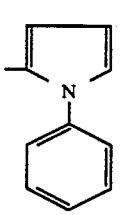 | 5 | Double bond |
| 131 | H | —COCH$_2$— | S | 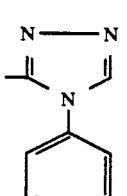 | 5 | Double bond |

| | | | | | | |
|---|---|---|---|---|---|---|
| 132 | H | —COCH$_2$— | S | ![triazole-N-phenyl with double bond] | 5 | Double bond |
| 133 | H | —COCH$_2$— | S | ![tetrazole-N-phenyl] | 5 | Single bond |
| 134 | H | —COCH$_2$— | S | ![tetrazole-N-phenyl isomer] | 5 | Single bond |
| 135 | H | —COCH$_2$— | S | ![imidazole-N-phenyl] | 5 | Double bond |
| 136 | H | —COCH$_2$— | S | ![pyrazole-N-phenyl] | 5 | Double bond |
| 137 | H | —COCH$_2$— | S | ![tetrazole-N-phenyl] | 6 | Single bond |
| 138 | H | —COCH$_2$— | S | imidazole-CH$_2$CH(NH$_2$)COOH | 6 | Single bond |
| 139 | H | —COCH$_2$— | S | imidazole with CH$_3$ and CH$_2$COOH | 6 | Single bond |

TABLE 4-continued

| 140 | H | —COCH$_2$— | S | (structure) | 6 | Single bond |

Structure: N=C(CH$_3$)-NH-C(CH$_3$)=C(CH$_2$N(CH$_3$)$_2$)- (pyrrole-type ring)

*Side-chain: —Z—A—(X)$_n$—R

| Example No. | Crystal form (Recrystallization solvent) | Melting point (°C.) | Salt |
|---|---|---|---|
| 87 | Light yellow needles (Dimethylformamide-water) | 193.0 (decomp.) | — |
| 88 | Yellow needles (Ethanol) | 197.0–198.5 | — |
| 89 | Yellow needles (Ethanol-diethyl ether) | 201.0–204.0 | — |
| 90 | Light yellow needles (Ethanol-n-hexane) | 162.0–163.0 | — |
| 91 | White powder (Ethyl acetate) | 100.0–102.0 | — |
| 92 | White powder (Ethyl acetate) | 74.0–80.0[2] | — |
| 93 | Colorless flakes (Ethanol) | 195.5–197.5 | — |
| 94 | Colorless needles (Ethanol-n-hexane) | 197.0–198.5 | — |
| 95 | Colorless prisms (Ethanol) | 193.0–194.0 | — |
| 96 | White powder (Ethanol) | 201.0–202.0 | — |
| 97 | Light yellow powder (Methanol-water) | 185.0–188.0 | — |
| 98 | White powder (Chloroform) | 195 (decomp.) | — |
| 99 | Light yellow granules (Ethanol-chloroform) | 199–201 | — |
| 100 | Light yellow prisms (Ethanol) | 146.5–148.0 | — |
| 101 | Colorless needles (Ethyl acetate-n-hexane) | 165.5–166.0 | — |
| 102 | Light brown needles (Dimethylformamide-water) | 220–221 | — |
| 103 | Light yellow prisms (Ethanol-n-hexane) | 144.0–144.5 | — |
| 104 | Light yellow powder (Methanol) | 215.0–216.0 (decomp.) | — |
| 105 | Light yellow needles (Ethanol-water) | 207.0–209.5 (decomp.) | — |
| 106 | Light brown granules (Dimethylformamide-water) | 202–204 (decomp.) | — |
| 107 | Light brown granules (Dimethylformamide-methanol) | 146–147.5 | — |
| 108 | Light brown needles (Methanol) | 227–228 | — |
| 109 | Colorless needles (Chloroform-ethanol-n-hexane) | 186.5–188.0 | — |
| 110 | Colorless needles (Methanol) | 219–220 | — |
| 111 | Yellow powder (Dimethylformamide) | 231.0–234.0 (decomp.) | — |
| 112 | Colorless needles (Chloroform-methanol-n-hexane) | 220.0–222.5 (decomp.) | — |
| 113 | Colorless needles (Chloroform-methanol-n-hexane) | 210.0–211.0 (decomp.) | — |
| 114 | Colorless needles (Ethanol) | 137.0–138.0 | — |
| 115 | Colorless needles (Methanol) | 211.0–212.0 | — |
| 116 | Colorless needles (Ethanol) | 186.0–187.0 (decomp.) | — |
| 117 | Colorless needles (Ethanol-water) | 207.0–208.0 | — |
| 118 | Colorless needles (Chloroform-methanol) | 244.0–247.0 (decomp.) | — |
| 119 | Yellow needles (Methanol-water) | 255.0–257.0 (decomp.) | — |
| 120 | Light brown powder (Chloroform-methanol-diethyl ether) | 185.5–186.5 (decomp.) | — |
| 121 | Colorless granules (Dichloromethane-n-hexane) | 119–120 | — |
| 122 | White powder (Chloroform-methanol) | 195–196 (decomp.) | — |

TABLE 4-continued

| | | | |
|---|---|---|---|
| 123 | Light brown powder (Ethyl acetate-ethanol) | 185–187 | — |
| 124 | Light yellow (Dimethylformamide-water) | 218–219 (decomp.) | — |
| 125 | Light brown prisms (Dimethylformamide-water) | 168–170 | — |
| 126 | Yellow powder (Dimethylformamide-water) | 196.5–198 (decomp.) | — |
| 127 | Light yellow powder (Chloroform-diethyl ether) | 170–172 | — |
| 128 | Light yellow powder (Dimethylformamide-water) | 196.5–197.0 (decomp.) | — |
| 129 | Yellow plates (Chloroform-methanol-diethyl ether) | 227–229 (decomp.) | — |
| 130 | Light brown needles (Dichloromethane-n-hexane) | 145–146 | $R^2$=$OCH_3$ (8-position) |
| 131 | Light brown powder (Ethanol) | 272–275 (decomp.) | $R^2$=OH (8-position) $H_2O$ |
| 132 | Colorless needles (Dimethylformamide) | 253–255 (decomp.) | $R^2$=$OCH_3$ (8-position) |
| 133 | Colorless needles (Ethanol) | 237–238 (decomp.) | $R^2$=OH (8-position) |
| 134 | Colorless needles (Ethanol-dimethylformamide) | 208–210 (decomp.) | $R^2$=$OCH_3$ (8-position) |
| 135 | Light brown powder (Chloroform) | 256–257 | $R^2$=OH (8-position) |
| 136 | Light yellow needles (Dimethylformamide-water) | 219–220 (decomp.) | $R^2$=$OCH_3$ (8-position) |
| 137 | Light yellow powder (Dimethylformamide) | Higher than 257 (decomp.) | $R^2$=OH (7-position) |
| 138 | Light yellow powder (Water) | higher than 195 | — |
| 139 | Light brown powder (Ethanol) | Higher than 245 (decomp.) | HCl |
| 140 | Light yellow powder (Diethyl ether) | 165–175 | — |

[2]NMR (CDCl₃) δ: 1.87–2.30 (2H, m), 2.46–2.75 (2H, tripletoid m), 2.80–3.10 (2H, tripletoid m), 3.10–3.67 (2H, m), 4.74–4.97 (1H, dd, J=9Hz, 4.5Hz), 6.73 (1H, d, J=9Hz), 7.07–7.75 (10H, m), 8.47–8.80 (1H, broad)

EXAMPLE 141

To a solution of 2 g (6.6 mM) of 6-[3-(2-imisazolyl)-thiopropoxy]-3,4-dihydrocarbostyril with 50 ml of DMF was added 520 mg (7.9 mM) of potassium hydroxide and the mixture was stirred at room temperature for 20 minutes. Next, to this reaction mixture was added dropwise 1.5 ml (19.8 mM) of ethyl bromide under ice-cooling condition. The reaction mixture was stirred at 49°–50° C. for 10 minutes. The reaction mixture was concentrated under reduced pressure to remove the solvent by evaporation. To this residue was added water, then extracted with chloroform, the chloroform extract was washed with water, and dried with anhydrous sodium sulfate and concentrated by removing the solvent. The residue thus obtained was purified by means of a silica gel column chromatography (eluent: chloroform:methanol:ethyl acetate=10:1:20), then recrystallized from ethanol-n-hexane to yield 1.2 g of 6-[3-(1-ethyl-2-imidazolyl)thiopropoxy]-3,4-dihydrocarbostyril. Colorless needle-like crystals.

Melting point: 120.5°–121.0° C.

By using suitable starting materials and by procedures similar to those described in Example 108, there were prepared compounds of Examples 13, 15, 25, 29, 30, 31, 32, 35, 38–40, 42, 55–65, 85–103, 107, 109–110, 112–137, as well as there were prepared compounds of Examples 173–179, 182, 185–188, 190, 191, 195–199 and 202.

EXAMPLE 142

To a solution of 2 g (5.5 mM) of 6-[2-(1-phenyl-2-imidazolyl)thioacetyl]-3,4-dihydrocarbostyril with 80 ml of a mixture of DMF:methanol=3:1 was added 208 mg (5.5 mM) of sodium borohydride, and the mixture was heated at 50°–60° C. for 1 hour with stirring. The reaction mixture was concentrated by removing the solvent, and the residue was poured in 50 ml of 1N-hydrochloric acid. The mixture was made alkanline with 1N-sodium hydroxide aqueous solution, then the crystals formed were collected by filtration, washed with water, and dried. Recrystallization from ethanol to yield 1.5 g of 6-[1-hydroxy-2-(1-phenyl-2-imidazolyl)-thioethyl]-3,4-dihydrocarbostyril. Yellow needle-like crystals.

Melting point: 197.0°–198.5° C.

By using suitable starting materials, and by procedures similar to those described in Example 142, there were prepared compounds of the above-mentioned Examples 91 and 92, as well as compounds of Examples 172, 185 and 190.

EXAMPLE 143

To 3 g of N'-cyclohexylcarbonyl-4-[6-(1,2-dihydro-2-oxoquinolyloxy]butyrohydrazide was added 120 g of polyphosphoric acid, and the mixture was heated at 190°–210° C. in an oil bath for 10 minutes with stirring. After cooled the reaction mixture, the mixture was poured in 400 ml of ice-water, then extracted with chloroform. The chloroform layer was washed with water and dried with anhydrous sodium sulfate. The dried extract was concentrated, and the residue was purified by means of a silica gel column chromatography (eluent: chloroform: methanol=20:1). Recrystallized from chloroform-petroleum ether to yield 0.4 g of 6-[3-(2-cyclohexyl-1,3,4-oxadiazol-5-yl)propoxy]carbostyril.

Yellow needle-like crystals.

Melting point: 160.°–161.5° C.

By using suitable starting materials, and by procedures similar to those described in Example 143, there was prepared compound of Example 4, as well as prepared compounds of Examples 150–166.

EXAMPLE 144

To a solution of 2 g (7.35 mM) of 6-[3-(1,2,4-triazol-1-yl)propoxy]-3,4-dihydrocarbostyril with 20 ml of DMF was added 350 mg (8.8 mM) of sodium hydride (60% in oil) and the mixture was heated at 60° C. for 30 minutes. Then under ice-cooling condition, 0.6 ml (8.1 mM) of ethyl bromide was added dropwise, further the reaction mixture was stirred at room temperature for 3 hours. To the reaction mixture was added water, then extracted with chloroform, the chloroform layer was washed with water, dried with anhydrous sodium sulfate, and concentrated by removing the solvent by evaporation. The resulting residue was purified by means of a silica gel column chromatography (eluent: dichloromethane:methanol =30:1), then recrystallized from ethyl acetate-n-hexane to yield 1.8 g of 1-ethyl-6-[3-(1,2,4-triazol-1-yl)propoxy] -3,4-dihydrocarbostyril. Colorless needle-like crystals.

Melting point: 97.0°–98.0° C.

By using a suitable starting material, and by procedures similar to those described in Example 144, there were prepared compounds of Examples 44 and 100.

EXAMPLE 145

3.63 Grams (10 mM) of 6-[2-(1-phenyl-2-imidazolyl)thioacetyl]-3,4-dihydrocarbostyril and 1.09 g (15 mM) of hydroxylamine hydrochloride were suspended in a mixture of 100 ml of ethanol with 20 ml of water, then 2.0 g (50 mM) of sodium hydroxide powder was added with stirring vigorously and further stirred at room temperature for 30 minutes. After the reaction was completed, the reaction mixture was neutralized with 5%-hydrochloric acid, and extracted with chloroform:methanol=8:1 mixture and the extract was dried with anhydrous magnesium sulfate, then concentrated by removing the solvent. The residue was purified by means of a silica gel column chromatography (eluent: chloroform: methanol=20:1), then recrystallized from ethanol to yield 3.34 g of 6-[1-hydroxyimino-2-(1-phenyl-2-imidazolyl)thioethyl]-3,4-dihydrocarbostyril. White powdery substance.

Melting point: 201.0°–202.0° C.

EXAMPLE 146

3.0 Grams (8.17 mM) of 6-[1-hydroxy-2-(1-phenyl-2-imidazolyl)thioethyl]-3,4-dihydrocarbostyril was added in 9 ml of thionyl chloride at −10° C., and stirred at the same temperature for 30 minutes. Then 50 ml of methanol was added dropwise to the reaction mixture and stirred at room temperature for 30 minutes. After the reaction was completed, the reaction mixture was made an alkaline with sodium hydrogen carbonate, then extracted with chloroform. The extract was dried with anhydrous magnesium sulfate, and concentrated by removing the solvent. The residue was recrystallized from ethanol to yield 1.5 g of 6-[1-methoxy-2-(1-phenyl-2-imidazolyl)-3,4-dihydrocarbostyril. Colorless prism-like crystals.

Melting point: 193.0°–194.0° C.

EXAMPLE 147

4.47 Grams (12.3 mM) of 6-[2-(1-phenyl-2-imidazolyl)thioacetyl]-3,4-dihydrocarbostyril was dissolved in 200 ml of chloroform and 45 ml of acetic acid, then under ice-cooling condition, 3.0 g (15.0 mM) of m-chlorobenzoic acid was added thereto, and stirred at the same temperature for 1 hour. After the reaction was completed, the reaction mixture was made an alkaline with sodium hydrogen carbonate and extracted with chloroform. The crystals formed in the chloroform layer were collected by filtration, washed with ethanol to yield 4.0 g of 6-[2-(1-phenyl-2-imidazolyl)sulfinylacetyl]-3,4-dihydrocarbostyril. White powdery substance.

Melting point: 195° C. (decomp.)

By using suitable starting materials and by procedures similar to those described in Example 147, there were prepared compounds of Examples 191, 193, 196, 199–200.

EXAMPLE 148

3.79 Grams (10 mM) of 6-[2-(1-phenyl-2-imidazolyl)-sulfinylacetyl]-3,4-dihydrocarbostyril was dissolved in a mixture of 240 ml of acetic acid with 100 ml of water, then 5.06 g (32 mM) of potassium permanganate was added thereto. This mixture was stirred at room temperature for 2 days. After the reaction was completed, chloroform was added to the reaction mixture and filtered with Celite (a trademark for distomaceous earth product, manufactured by Johns-Manville Products Corp.). The filtrate was washed with water and dried with anhydrous magnesium sulfate. The residue obtained by removing the solvent was purified by means of a silica gel column chromatography (eluent: chloroform : methanol=30:1), and recrystallized from ethanol-chloroform to yield 0.6 g of 6-[2-(1-phenyl-2-imidazolyl)sulfonylacetyl]-3,4-dihydrocarbostyril. Light yellow granular substance.

Melting point: 199°–201° C.

By using suitable starging materials, and by procedures similar to those described in Example 148, there were prepared compounds of Examples 194, 195, 197, 201 and 202.

EXAMPLE 149

To a solution of 60 ml of carbon disulfide with 23.3 g (0.096 M) of 2-(1-phenyl-2-imidazolyl)thioacetyl chloride and 12.8 g (0.096 M) of aluminum chloride was added gradually 3.5 g (0.024 M) of 3,4-hydrocarbostyril at room temperature under stirring condition. After the addition was finished, the reaction mixture was refluxed by heating for 2.5 hours. Carbon disulfide was removed by decantation, and the residue was poured in ice-water. The crystals formed were collected by filtration, and recrystallized from ethanol to yield 17 g of 6-[2-(1-phenyl-2-imidazolyl)thioacetyl]-3,4-dihydrocarbostyril. Light yellow needle-like crystals.

Melting point: 209.0°–210.0° C.

By using suitable starting materials and by using procedures similar to those described in Example 149, there were prepared compounds of Examples 69–84, 86–87, 89–90, 93–94 and 97–140. As well as there were prepared compounds of Examples 171, 173, 174, 175–184, 186, 187–189, 191–202.

TABLE 5

| Example No. | R¹ | —Z—A— | (X)ₙ | R | R² | Position of the side-chain | 3,4-carbon-carbon bond | Crystal form (Recrystallization solvent) | Melting point (°C.) | Salt |
|---|---|---|---|---|---|---|---|---|---|---|
| 150 | H | —O(CH₂)₃— | — |  | H | 6 | Single bond | Colorless powder (Chloroform-diethyl ether) | 85–90 | |
| 151 | H | —O(CH₂)₃— | — |  | H | 3 | Double bond | Colorless powder (Chloroform-diethyl ether) | 184–185.5 | |
| 152 | H | —O(CH₂)₃— | — |  | H | 4 | Double bond | Colorless powder (Chloroform-diethyl ether) | 209–212 | |
| 153 | H | —O(CH₂)₃— | — |  | H | 5 | Single bond | Colorless powder (Chloroform-diethyl ether) | 193–194 | |
| 154 | H | —O(CH₂)₃— | — |  | H | 7 | Single bond | Colorless powder (Chloroform-diethyl ether) | 152–153.5 | — |
| 155 | H | —O(CH₂)₃— | — |  | H | 8 | Single bond | Colorless plates (Chloroform-diethyl ether) | 131.5–133 | — |

TABLE 5-continued

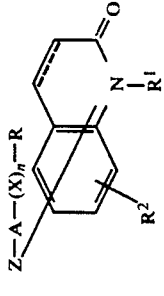

| Example No. | R¹ | —Z—A— | (X)ₙ | R | R² | Position of the side-chain | 3,4-carbon-bond | Crystal form (Recrystallization solvent) | Melting point (°C.) | Salt |
|---|---|---|---|---|---|---|---|---|---|---|
| 156 | H | —O(CH₂)₃— | — | 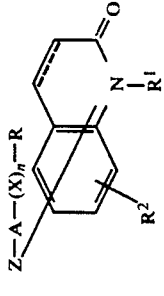 | H | 5 | Double bond | Colorless powder (Chloroform-diethyl ether) | 217–219 | — |
| 157 | H | —O(CH₂)₃— | — |  | H | 7 | Double bond | Colorless powder (Chloroform-diethyl ether) | 148.5–149.5 | — |
| 158 | H | —O(CH₂)₃— | — | 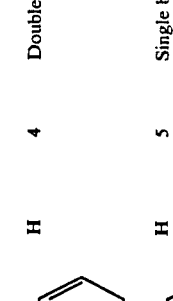 | H | 8 | Double bond | Colorless powder (Chloroform-diethyl ether) | 145–146.5 | — |
| 159 | H | —O(CH₂)₃— | — |  | H | 3 | Double bond | Colorless powder (Chloroform-diethyl ether) | 160–161.5 | — |
| 160 | H | —O(CH₂)₃— | — | 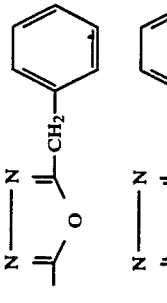 | H | 4 | Double bond | Colorless powder (Chloroform-diethyl ether) | 194.5–197.0 | — |
| 161 | H | —O(CH₂)₃— | — | 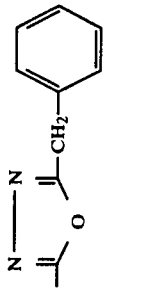 | H | 5 | Single bond | Colorless powder (Chloroform-diethyl ether) | 153.5–154.5 | — |
| 162 | H | —O(CH₂)₃— | — |  | H | 7 | Single bond | Colorless powder (Chloroform-diethyl ether) | 115–116 | — |

TABLE 5-continued

| Example No. | $R^1$ | —Z—A— | $(X)_n$ | R | $R^2$ | Position of the side-chain | 3,4-carbon-carbon bond | Crystal form (Recrystallization solvent) | Melting point (°C.) | Salt |
|---|---|---|---|---|---|---|---|---|---|---|
| 163 | H | —O(CH$_2$)$_3$— | — | 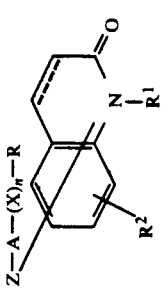 | H | 8 | Single bond | Colorless plates (Chloroform-diethyl ether) | 113.5–114.5 | — |
| 164 | H | —O(CH$_2$)$_3$— | — | 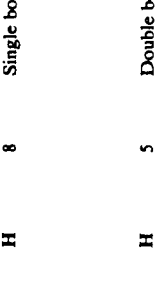 | H | 5 | Double bond | Colorless powder (Chloroform-diethyl ether) | 169–170 | — |
| 165 | H | —O(CH$_2$)$_3$— | — | 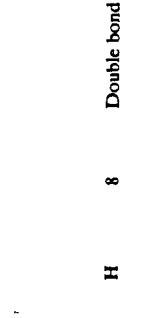 | H | 7 | Double bond | Colorless powder (Chloroform-diethyl ether) | 162–165 | — |
| 166 | H | —O(CH$_2$)$_3$— | — | 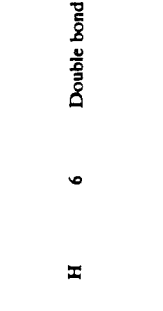 | H | 8 | Double bond | Colorless powder (Chloroform-diethyl ether) | 142–143.5 | — |
| 167 | H | —O(CH$_2$)$_3$— | — |  | H | 6 | Single bond | Colorless needles (Dichloromethane-n-hexane) | 121–122 | — |
| 168 | H | —O(CH$_2$)$_3$— | — |  | H | 6 | Double bond | Colorless needles (Dichloromethane-diethyl ether) | 172–174.5 | — |

TABLE 5-continued
| Example No. | R¹ | —Z—A— | (X)ₙ | R | R² | Position of the side-chain | 3,4-carbon-carbon bond | Crystal form (Recrystallization solvent) | Melting point (°C.) | Salt |
|---|---|---|---|---|---|---|---|---|---|---|
| 169 | H | —O(CH₂)₃— | — | 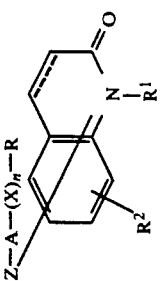 | H | 6 | Single bond | Colorless powder (Chloroform-methanol) | 227–228 | — |
| 170 | H | —O(CH₂)₃— | — | —N⎯⎯N⎯⎯⫽N | H | 7 | Double bond | Colorless needles (Ethanol-n-hexane) | 193.0–195.5 | — |

EXAMPLES 171-174

By using suitable starting materials and unsing procedures similar to those described in Example 69, there were prepared compounds of Examples 171-174 as shown in Table 6 as follows.

TABLE 6

[Structure: Z—A—(X)n—R with bicyclic ring system bearing R² and N—R¹ with C=O]

| Example No. | R¹ | —Z—A— | (X)n | R | R² | Position of the side-chain | 3,4-carbon-carbon bond | Crystal form (Recrystallization solvent) | Melting point (°C.) | Salt |
|---|---|---|---|---|---|---|---|---|---|---|
| 171 | H | —COCH₂— | — | [N-linked dihydro-oxazole with CH₃] | 8-OCH₃ | 5 | Double bond | Light brown powder (Ethanol) | 224–226 | — |
| 172 | H | —CHCH₂—  \|  OH | — | [N-linked dihydro-oxazole with CH₃] | H | 6 | Single bond | Colorless powder (Ethanol-diethyl ether) | 129–130 (decomp.) | — |
| 173 | H | —COCH₂CH₂— | — | [thiazole linked to pyridine] | H | 6 | Single bond | Colorless powder (Chloroform-methanol-diethyl ether) | 236–237 (decomp.) | — |
| 174 | H | —COCH₂CH₂— | — | [N-phenyl thiadiazole] | H | 6 | Single bond | Light yellow plates (Dimethylformamide-water) | 220–221 | — |

EXAMPLES 175-202

By using suitable starting materials and by using procedures similar to those described in Examples 85 and 86, there were prepared compounds of Examples 175-202 as shown in Table 7 as follows.

TABLE 7

$$Z-A-(X)_n-R$$

(structure: bicyclic ring system with N-R¹, C=O, and R² substituent)

| Example No. | R¹ | —Z—A— | (X)ₙ | R | R² | Position of the side-chain | 3,4-carbon-carbon bond | Crystal form (Crystallization solvent) | Melting point (°C.) | Salt |
|---|---|---|---|---|---|---|---|---|---|---|
| 175 | H | —COCH₂— | —S— | (imidazole)-N-CH₃CHCOOH | H | 6 | Single bond | Light yellow powder (Acetone-water) | 210.5–212.5 | HCl.½H₂O |
| 176 | H | —COCH₂— | —S— | (imidazole)-N-CH₃CHCOOC₂H₅ | H | 6 | Single bond | Light yellow powder (Acetone-n-hexane) | 123.0–125.0 | — |
| 177 | H | —COCH₂— | —S— | (imidazole)-N-(C₆H₄)-COOH | H | 6 | Single bond | Colorless powder (Ethanol-water) | 194.5–199.0 | 2H₂O |
| 178 | H | —COCH₂— | —S— | (imidazole)-N-phenyl | 8-F | 6 | Single bond | (Recrystallization solvent) Colorless powder (Ethanol-water) | 205.5–208.5 | — |

TABLE 7-continued

[Structure: Z—A—(X)ₙ—R attached to bicyclic ring system with N—R¹, C=O, and R² substituent]

| Example No. | R¹ | —Z—A— | (X)ₙ | R | R² | Position of the side-chain | 3,4-carbon-carbon bond | Crystal form | Melting point (°C.) | Salt |
|---|---|---|---|---|---|---|---|---|---|---|
| 179 | H | —COCH₂— | —S— | [pyrrole-O-SO₂-(p-tolyl)] | H | 6 | Single bond | Colorless needles (Dichloromethane-n-hexane) | 208–209 | — |
| 180 | H | —COCH₂— | —O— | [CH₃-C=CH-C(CH₃)=N-NH] (pyrazole) | H | 6 | Single bond | Light yellow powder (Chloroform-methanol-diethyl ether) | NMR³ | — |
| 181 | H | —COCH₂— | —S— | [CH₃-C=CH-C(CH₃)=N-NH] (pyrazole) | H | 6 | Single bond | Colorless powder (Chloroform-methanol-diethyl ether) | NMR⁴ | HCl |
| 182 | H | —COCH₂— | —O— | [N=N-C(=N-phenyl)] | H | 6 | Single bond | Light brown plates (Dimethylformamide-water) | 250–251 (decomp.) | — |
| 183 | H | —COCH₂— | —S— | [COOC₂H₅, CH₃ substituted pyrazole-NH] | H | 6 | Single bond | Light brown powder (Dimethylformamide-water) | NMR⁵ | — |

TABLE 7-continued

[Structure: Z—A—(X)ₙ—R attached to a bicyclic ring system with C=O and N-R¹ group, R² substituent]

| Example No. | R¹ | —Z—A— | (X)ₙ | R | R² | Position of the side-chain | 3,4-carbon-carbon bond | Crystal form | Melting point (°C.) | Salt |
|---|---|---|---|---|---|---|---|---|---|---|
| 184 | H | —COCH₂— | —S— | [heterocycle with COOH, CH₃, NH] | H | 6 | Single bond | Light brown powder | 220–221 (decomp.) | H₂O |
| 185 | H | —CHCH₂CH₂—<br>     \|<br>    OH | —S— | [triazole-phenyl] | H | 6 | Single bond | Colorless prisms (Ethanol) | 156–157 | — |
| 186 | H | —COCH₂— | —S— | [triazole-CH₂CH₂-catechol] | H | 6 | Single bond | Colorless powder (Chloroform-methanol) | 199–200 | — |
| 187 | H | —COCH₂— | —S— | [triazole-phenyl] | 8-OSO₂CH₃ | 5 | Double bond | Light brown flakes (Dimethylformamide-water) | 223 (decomp.) | — |

TABLE 7-continued

Structure: Z—A—(X)$_n$—R on quinolinone scaffold with R$^2$ substituent and N—R$^1$

| Example No. | R$^1$ | —Z—A— | (X)$_n$ | R | R$^2$ | Position of the side-chain | 3,4-carbon-carbon bond | Crystal form | Melting point (°C.) | Salt |
|---|---|---|---|---|---|---|---|---|---|---|
| 188 | H | —COCH$_2$— | —S— |  | 8-OH | 5 | Double bond | Light yellow crystals (Dimethylformamide-water) | 221 (decomp.) | — |
| 189 | H | —COCH$_2$— | —S— |  | H | 6 | Single bond | Light brown powder (Dimethylformamide-water) | 223–224 (decomp.) | — |
| 190 | H | —CHCH$_2$—<br>\|<br>OH | —S— |  | H | 6 | Single bond | Colorless needles (Dimethylformamide-water) | 217–218 (decomp.) | — |
| 191 | H | —COCH$_2$— | —S=O |  | H | 6 | Single bond | Light yellow powder (Dimethylformamide-water) | 153.0–156.0 (decomp.) | — |

TABLE 7-continued

| Example No. | R¹ | −Z−A− | (X)ₙ | R | R² | Position of the side-chain | 3,4-carbon bond | Crystal form | Melting point (°C.) | Salt |
|---|---|---|---|---|---|---|---|---|---|---|
| 192 | H | −CO(CH₂)₃− | −S− | pyridyl | H | 6 | Single bond | Colorless powder (Dimethylformamide-water) | 163.0–165.5 (decomp.) | — |
| 193 | H | −CO(CH₂)₃− | −S(=O)− | pyridyl | H | 6 | Single bond | Colorless powder (Methanol) | 182.5–183.5 (decomp.) | — |
| 194 | H | −CO(CH₂)₃− | −S(=O)₂− | pyridyl | H | 6 | Single bond | Colorless powder (Methanol) | 189.0–190.5 (decomp.) | — |
| 195 | H | −COCH₂− | −S(=O)₂− | N-phenyltriazolyl | H | 6 | Single bond | Light yellow powder (Dimethylformamide-water) | 194.5–198.0 (decomp.) | — |
| 196 | H | −COCH₂− | −S(=O)− | N-cyclohexyltriazolyl | H | 6 | Single bond | Light yellow powder (Dimethylformamide-water) | 151.0–155.0 (decomp.) | — |

TABLE 7-continued structure: Z—A—(X)ₙ—R with bicyclic system bearing N—R¹ and =O, R² substituent

| Example No. | R¹ | —Z—A— | (X)ₙ | R | R² | Position of the side-chain | 3,4-carbon-carbon bond | Crystal form | Melting point (°C.) | Salt |
|---|---|---|---|---|---|---|---|---|---|---|
| 197 | H | —COCH₂— | O=S=O | N=N ring with N-cyclohexyl | H | 6 | Single bond | Colorless powder (Chloroform-methanol) | 156.0–157.0 (decomp.) | — |
| 198 | H | —COCH₂— | —S— | N=N ring with N—CH₃ | H | 6 | Single bond | Yellow powder (Dimethylformamide-water) | 192.5–194.0 (decomp.) | — |
| 199 | H | —COCH₂— | —S=O | N=N ring with N—CH₃ | H | 6 | Single bond | Yellow powder (Dimethylformamide-water) | 170.0–171.5 (decomp.) | — |
| 200 | H | —COCH₂— | —S=O | pyridyl | H | 6 | Single bond | Yellow powder (Dimethylformamide) | 200.0–201.0 (decomp.) | — |
| 201 | H | —COCH₂— | O=S=O | pyridyl | H | 6 | Single bond | Yellow needles (Dimethylformamide-water) | 219.5–220.0 (decomp.) | — |

TABLE 7-continued

[Structure: Z—A—(X)$_n$—R attached to a bicyclic ring system with N—R$^1$, C=O, and R$^2$ substituent]

| Example No. | R$^1$ | —Z—A— | (X)$_n$ | R | R$^2$ | Position of the side-chain | 3,4-carbon-carbon bond | Crystal form | Melting point (°C.) | Salt |
|---|---|---|---|---|---|---|---|---|---|---|
| 202 | H | —COCH$_2$— | $-\overset{O}{\underset{O}{S}}-$ | [N=N heterocycle with N—CH$_3$] | H | 6 | Single bond | Colorless powder (Dimethylformamide-water) | 201.0–202.5 | — |

NMR$^3$ (DMSO-d$_6$): 2.7(3H, s), 2.37–2.72(tripletoid m, 2H), 2.80–3.15(2H, tripletoid m), 5.38(2H, s), 5.33(1H, s), 6.93(1H, J=9Hz), 7.67–8.10(2H, m), 10.5. (1H, s), 9.67–11.00(1H, broad).
NMR$^4$ (DMSO-d$_6$): 1.90–2.14(3H, s of two peaks), 2.40–2.70(2H, tripletoid m), 2.80–3.12(2H, tripletoid m), 4.40–4.72(2H, broad), 6.52–6.90(2H, broad), 6.96(1H, d, J=8.8Hz), 7.72–7.96(2H, m), 10.48(1H, s), 11.84–12.22(1H, broad two peaks).
NMR$^5$ (DMSO-d$_6$): 1.27(3H, tripletoid m), 2.24–2.96(3H, two peaks), 2.46–2.64(2H, tripletoid m), 2.84–3.08(2H, tripletoid m), 4.06–4.34(2H, quartetoid m), 4.52–4.92(2H, two peaks) 6.96(1H, d, J=8.8Hz), 8.70–8.94(2H, m).

What is claimed is:

1. A carbostyril compound or pharmaceutically acceptable salt thereof represented by the formula 1a,

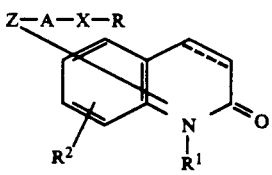 (1a)

wherein
R is unsubstituted imidazolyl or imidazolyl having 1 to 3 substituents, on the heterocyclic residual ring, selected from phenyl; phenyl having 1 to 3 substituents selected from lower alkyl, halo-lower alkyl, halogen, hydroxy, amino, lower alkylamino, carboxy and lower alkoxy; cycloalkyl; phenylthio; lower alkyl; lower alkyl having 1 to 2 substituents selected from amino, lower alkylamino and carboxyl; amino; hydroxyl; cyano; carboxyl; lower alkoxycarbonyl; phenyl-lower alkyl; phenyl-lower alkyl having hydroxyl substituents on the phenyl ring; phenylsulfonyl; phenylsulfonyl having lower alkyl substituents on the phenyl ring; lower alkoxysubstituted phenyl-lower alkyl; lower alkylthio; lower alkenyl; lower alkoxy and pyridyl;
$R^1$ is hydrogen, lower alkyl or phenyl-lower alkyl;
$R^2$ is hydrogen, halogen, lower alkyl-sulfonyloxy, lower alkoxy or hyroxyl;
Z is oxygen, sulfur,

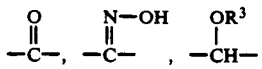

wherein $R^3$ is hydrogen or lower alkyl, or —NH—;
A is lower alkylene;
X is sulfur, —SO— or —SO$_2$—; and
the carbon-carbon bond between the 3- and 4-positions in the carbostyril skeleton is a single or double bond.

2. The carbostyril compound or pharmaceutically acceptable salt thereof according to claim 1, wherein Z is oxygen or sulfur.

3. The carbostyril compound of pharmaceutically acceptable salt thereof according to claim 1, wherein Z is

4. The carbostyril compound or pharmaceutically acceptable salt thereof according to claim 1, wherein Z is

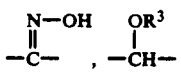

wherein $R^3$ is the same as defined in claim 1, or —NH—.

5. The carbostyril compound or pharmaceutically acceptable salt thereof according to claim 1, wherein R is imidazolyl or imidazolyl having substituents selected from phenyl; phenyl having 1 to 3 substituents, on the phenyl ring, selected from lower alkyl, halo-lower alkyl, halogen, hydroxy, amino, lower alkylamino, carboxyl and lower alkoxy; cycloalkyl; phenylthio; lower alkyl; lower alkyl having 1 to 2 substituents selected from amino, lower alkylamino and carboxyl; amino; hydroxyl; cyano; carboxyl; lower alkoxycarbonyl; phenyl-lower alkyl; phenyl-lower alkyl having hydroxyl substituents on the phenyl ring; phenyl sulfonyl; phenylsulfonyl having lower alkyl substituents on the phenyl ring; lower alkoxy-substituted phenyl-lower alkyl; lower alkylthio; lower alkenyl; lower alkoxy and pyridyl.

6. The carbostyril compound or pharmaceutically acceptable salt thereof according to claim 5, wherein $R^1$ is hydrogen.

7. The carbostyril compound or pharmaceutically acceptable salt thereof according to claim 5, wherein $R^1$ is lower alkyl or phenyl-lower alkyl.

8. The carbostyril compound or pharmaceutically acceptable salt thereof according to claim 6, wherein $R^2$ is hydrogen.

9. The carbostyril compound or pharmaceutically acceptable salt thereof according to claim 8, wherein the side-chain —Z—A—X—R is substituted at the 6- or 7-position in the carbostyril skeleton.

10. The carbostyril compound or pharmaceutically acceptable salt thereof according to claim 9, wherein the carbon-carbon bond between the 3- and 4-positions in the carbostyril skeleton is a single bond.

11. The carbostyril compound or pharmaceutically acceptable salt thereof according to claim 9, wherein the carbon-carbon bond between the 3- and 4-positions in the carbostyril skeleton is a double bond.

12. The carbostyril compound or pharmaceutically acceptable salt thereof according to claim 2, wherein Z is oxygen.

13. The carbostyril compound or pharmaceutically acceptable salt thereof according to claim 2, wherein X is sulfur.

14. The carbostyril compound or pharmaceutically acceptable salt thereof according to claim 3, wherein X is sulfur.

15. The carbostyril compound or pharmaceutically acceptable salt thereof according to claim 1, wherein R is imidazolyl or imidazolyl having 1 to 3 substituents selected from phenyl; phenyl having 1 to 3 substituents selected from lower alkyl, halolower alkyl, halogen, hydroxy, lower alkylamino, carboxyl and lower alkoxy; cycloalkyl; lower alkyl; lower alkyl having 1 to 2 substituents selected from amino, lower alkylamino and carboxyl; carboxyl; lower alkoxycarbonyl; phenyl-lower alkyl; lower alkenyl; and pyridyl.

16. A pharmaceutical composition for inhibiting adhesion of thrombocytes comprising, as active ingredient, a carbostyril compound represented by the formula (1a) according to claim 1 or pharmaceutically acceptable salt thereof, together with a pharmaceutically acceptable carrier.

17. The pharmaceutical composition according to claim 16, wherein the carbostyril compound is 6-{3-[1-(3-pyridyl)-2-imidazolyl]thiopropoxy}-3,4-dihydrocarbostyril.

18. The pharmaceutical composition according to claim 16, wherein the carbostyril compound is 6-[2-(1-phenyl-2-imidazolyl)thioacetyl]-3,4-dihydrocarbostyril.

* * * * *